(12) United States Patent
Webb et al.

(10) Patent No.: US 10,149,917 B2
(45) Date of Patent: Dec. 11, 2018

(54) FLUID COMPOSITION AND A MICROFLUIDIC DELIVERY CARTRIDGE COMPRISING THE SAME

(71) Applicant: The Procter & Gamble Company, Cincinnati, OH (US)

(72) Inventors: Kim Lynn Webb, Fairfield, OH (US); Dana Paul Gruenbacher, Fairfield, OH (US); Steven Anthony Horenziak, Cincinnati, OH (US); William Paul Mahoney, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/358,171

(22) Filed: Nov. 22, 2016

(65) Prior Publication Data

US 2018/0140733 A1 May 24, 2018

(51) Int. Cl.
| | | |
|---|---|---|
| *A61L 9/03* | (2006.01) | |
| *B05B 9/03* | (2006.01) | |
| *A61L 9/01* | (2006.01) | |
| *A61L 9/12* | (2006.01) | |
| *A61L 9/14* | (2006.01) | |
| *B05B 1/24* | (2006.01) | |

(52) U.S. Cl.
CPC .................. *A61L 9/03* (2013.01); *A61L 9/01* (2013.01); *A61L 9/12* (2013.01); *A61L 9/14* (2013.01); *B05B 1/24* (2013.01); *B05B 9/03* (2013.01); *A61L 2209/133* (2013.01)

(58) Field of Classification Search
CPC ........................................................ A61L 9/03
See application file for complete search history.

(56) References Cited

U.S. PATENT DOCUMENTS

| | | |
|---|---|---|
| 3,465,350 A | 9/1969 | Keur et al. |
| 3,465,351 A | 9/1969 | Keur et al. |
| 3,967,286 A | 6/1976 | Andersson et al. |
| 4,532,530 A | 7/1985 | Hawkins |
| 5,084,713 A | 1/1992 | Wong |
| 5,317,339 A | 5/1994 | Braun |
| 5,591,409 A | 1/1997 | Watkins |
| 5,610,635 A | 3/1997 | Murray |

(Continued)

FOREIGN PATENT DOCUMENTS

| | | |
|---|---|---|
| CA | 2 213 066 A1 | 2/1999 |
| CN | 1393491 A | 1/2003 |

(Continued)

OTHER PUBLICATIONS

All Office Actions for P&G Case 13412L; U.S. Appl. No. 14/310,401.

(Continued)

*Primary Examiner* — Arrie L Reuther
(74) *Attorney, Agent, or Firm* — Abbey A. Lopez

(57) ABSTRACT

A cartridge having a microfluidic die and a fluid composition in fluid communication with the microfluidic die is provided. The fluid composition includes from about 50% to about 100%, by weight of the fluid composition, of a perfume mixture, wherein the perfume mixture has a mol-weighted average C log P of less than or equal to about 2.9; a polyol; and from about 0.25 wt. % to about 9.5 wt. %, by weight of the fluid composition, of water.

20 Claims, 17 Drawing Sheets

(56) References Cited

U.S. PATENT DOCUMENTS

| | | |
|---|---|---|
| 5,666,140 A | 9/1997 | Mitani et al. |
| 5,714,989 A | 2/1998 | Wade et al. |
| 5,874,974 A | 2/1999 | Courian et al. |
| 5,975,675 A | 11/1999 | Kim |
| 6,010,210 A | 1/2000 | Wilson et al. |
| 6,012,799 A | 1/2000 | Silverbrook |
| 6,024,440 A | 2/2000 | Murthy et al. |
| 6,113,228 A | 9/2000 | Pawlowski |
| 6,126,277 A | 10/2000 | Feinn et al. |
| 6,139,131 A | 10/2000 | Prasad et al. |
| 6,170,937 B1 | 1/2001 | Childers et al. |
| 6,261,347 B1 | 7/2001 | Moreland |
| 6,282,458 B1 | 8/2001 | Muray et al. |
| 6,287,550 B1 | 9/2001 | Trinh |
| 6,322,200 B1 | 11/2001 | Feinn et al. |
| 6,325,475 B1 | 12/2001 | Hayes et al. |
| 6,371,451 B1 | 4/2002 | Choi |
| 6,543,887 B2 | 4/2003 | Chang |
| 6,672,129 B1 | 1/2004 | Frederickson et al. |
| 6,698,862 B1 | 3/2004 | Chol |
| 6,808,684 B2 | 10/2004 | Boden et al. |
| 6,834,937 B2 | 12/2004 | Killmeier |
| 7,097,263 B2 | 8/2006 | Silverbrook |
| 7,201,916 B2 | 4/2007 | Schiavo |
| 7,223,361 B2 | 5/2007 | Kvietok et al. |
| 7,293,849 B2 | 11/2007 | Tani et al. |
| 7,328,974 B2 | 2/2008 | Wang |
| 7,367,661 B2 | 5/2008 | Hess et al. |
| 7,389,943 B2 | 6/2008 | Jaworski |
| 7,490,815 B2 | 2/2009 | Tollens et al. |
| 7,499,632 B2 | 3/2009 | Granger |
| 7,669,978 B2 | 3/2010 | Spivey |
| 8,020,573 B2 | 9/2011 | Lamers et al. |
| 8,087,759 B2 | 1/2012 | Oikawa et al. |
| 8,101,124 B2 | 1/2012 | Uchiyama |
| 8,142,558 B2 | 3/2012 | Robertson et al. |
| 8,201,752 B2 | 6/2012 | Brodbeck |
| 8,251,500 B2 | 8/2012 | Yamanda et al. |
| 8,727,234 B2 | 5/2014 | Haran |
| 8,821,802 B2 | 9/2014 | Haran |
| 8,870,090 B2 | 10/2014 | Feriani |
| 8,881,999 B2 | 11/2014 | Blaylock et al. |
| 9,174,453 B1 | 11/2015 | Dodd et al. |
| 9,211,356 B2 | 12/2015 | Gruenbacher et al. |
| 9,211,980 B1 | 12/2015 | Gruenbacher |
| 9,377,786 B2 | 6/2016 | Nakamoto et al. |
| 9,554,459 B2 | 1/2017 | Gruenbacher et al. |
| 9,636,430 B2 | 5/2017 | Gruenbacher et al. |
| 2001/0050317 A1 | 12/2001 | Denen |
| 2002/0050533 A1 | 5/2002 | Hirota |
| 2002/0063752 A1 | 5/2002 | Clark |
| 2002/0086319 A1 | 7/2002 | Elison et al. |
| 2002/0192255 A1 | 12/2002 | Schiavo |
| 2003/0062385 A1 | 4/2003 | Engel |
| 2003/0218077 A1 | 11/2003 | Boticki |
| 2004/0119793 A1 | 6/2004 | Mutz et al. |
| 2004/0200907 A1 | 10/2004 | Martens et al. |
| 2004/0032468 A1 | 12/2004 | Killmeier et al. |
| 2005/0018016 A1 | 1/2005 | Silverbrook |
| 2005/0037945 A1 | 2/2005 | Gygax et al. |
| 2005/0062804 A1 | 3/2005 | Eaton |
| 2005/0077376 A1 | 4/2005 | Hess et al. |
| 2005/0091879 A1 | 5/2005 | DuVal et al. |
| 2005/0124512 A1 | 6/2005 | Woo et al. |
| 2005/0205916 A1 | 9/2005 | Conway et al. |
| 2005/0279854 A1 | 12/2005 | Martens et al. |
| 2006/0065755 A1 | 3/2006 | Sugita et al. |
| 2006/0152550 A1 | 7/2006 | Tomita |
| 2007/0008380 A1 | 1/2007 | Ushinohama |
| 2007/0010645 A1 | 1/2007 | Vonwiller et al. |
| 2007/0207174 A1 | 9/2007 | Pluyter |
| 2008/0023569 A1 | 1/2008 | O'Leary et al. |
| 2008/0043063 A1 | 2/2008 | Bergstedt |
| 2008/0061163 A1 | 3/2008 | Kubby et al. |
| 2008/0073443 A1 | 3/2008 | Tollens |
| 2008/0197213 A1 | 8/2008 | Flashinski et al. |
| 2009/0096839 A1 | 4/2009 | Olbrich et al. |
| 2009/0108094 A1 | 4/2009 | Irvi |
| 2009/0126722 A1 | 5/2009 | Sugita et al. |
| 2009/0289127 A1 | 11/2009 | Tollens |
| 2010/0001091 A1 | 1/2010 | Bara et al. |
| 2010/0154790 A1 | 6/2010 | Merassi et al. |
| 2010/0206306 A1 | 8/2010 | Feriani et al. |
| 2010/0328957 A1 | 12/2010 | Hessing |
| 2011/0024521 A1 | 2/2011 | Joergensen |
| 2011/0036365 A1 | 2/2011 | Chong et al. |
| 2011/0049266 A1 | 3/2011 | Joergensen |
| 2011/0089252 A1 | 4/2011 | Rosener et al. |
| 2011/0130877 A1 | 6/2011 | Lynch |
| 2011/0221083 A1 | 9/2011 | Laulicht |
| 2011/0284653 A1 | 11/2011 | Butler et al. |
| 2011/0284656 A1 | 11/2011 | Kambayashi et al. |
| 2011/0290911 A1 | 12/2011 | Tollens et al. |
| 2012/0093491 A1 | 4/2012 | Browder et al. |
| 2012/0097754 A1 | 4/2012 | Vlad et al. |
| 2013/0010035 A1 | 1/2013 | Norikane |
| 2013/0026250 A1 | 1/2013 | Burt |
| 2013/0206857 A1 | 8/2013 | Ivri |
| 2013/0292484 A1 | 11/2013 | Jackson |
| 2014/0078229 A1 | 3/2014 | Jackson et al. |
| 2014/0369895 A1 | 12/2014 | Turner et al. |
| 2015/0367013 A1 | 12/2015 | Gruenbacher et al. |
| 2015/0367014 A1 | 12/2015 | Gruenbacher et al. |
| 2015/0367016 A1 | 12/2015 | Gruenbacher et al. |
| 2015/0367356 A1* | 12/2015 | Gruenbacher et al. ... B05B 1/24 |
| 2015/0368001 A1 | 12/2015 | Gruenbacher et al. |
| 2016/0271639 A1 | 9/2016 | Bush et al. |
| 2016/0354799 A1 | 12/2016 | Gruenbacher et al. |
| 2017/0072085 A1 | 3/2017 | Gruenbacher et al. |
| 2017/0072086 A1 | 3/2017 | Gruenbacher et al. |
| 2017/0094720 A1 | 3/2017 | Gruenbacher et al. |
| 2017/0165390 A1 | 6/2017 | Gruenbacher et al. |

FOREIGN PATENT DOCUMENTS

| | | |
|---|---|---|
| CN | 1223637 C | 10/2005 |
| CN | 101 020 073 A | 8/2007 |
| CN | 204072869 U | 1/2015 |
| EP | 1510228 A1 | 3/2005 |
| EP | 1894727 A2 | 3/2008 |
| EP | 2143576 B1 | 11/2012 |
| GB | 2410468 A | 3/2005 |
| JP | H09123453 A | 5/1997 |
| JP | 2002254613 A | 9/2002 |
| JP | A-2004-311093 | 11/2004 |
| JP | 2005185366 A | 7/2005 |
| JP | A-2008-168223 | 7/2005 |
| JP | 2005224503 A | 8/2005 |
| JP | 2005224504 A | 8/2005 |
| JP | A2005224504 | 8/2005 |
| JP | 2007054446 A | 3/2007 |
| JP | A-2008-061937 | 3/2008 |
| JP | A-2009-213901 | 9/2009 |
| KR | 100238582 B1 | 1/2000 |
| WO | WO 01/30404 A1 | 5/2001 |
| WO | WO 2004/044552 A2 | 5/2004 |
| WO | WO 2006/004902 A1 | 1/2006 |
| WO | WO 2007/083164 A2 | 7/2007 |
| WO | WO 2014/043424 A1 | 3/2014 |
| WO | WO 2015/175527 A2 | 11/2015 |
| WO | WO 2015/195994 A1 | 12/2015 |

OTHER PUBLICATIONS

All Office Actions for P&G Case 13413L; U.S. Appl. No. 14/310,285.
All Office Actions for P&G Case 13413CL; U.S. Appl. No. 14/950,214.
All Office Actions for P&G Case 13414L; U.S. Appl. No. 14/310,311.
All Office Actions for P&G Case 13415L; U.S. Appl. No. 14/310,334.
All Office Actions for P&G Case 13416L; U.S. Appl. No. 14/310,367.
All Office Actions for P&G Case 12593; U.S. Appl. No. 14/024,673.
All Office Actions for P&G Case 13267; U.S. Appl. No. 14/217,524.
All Office Actions for P&G Case 13729; U.S. Appl. No. 14/658,280.
All Office Actions for P&G Case 13412C; U.S. Appl. No. 15/231,807.

(56) References Cited

OTHER PUBLICATIONS

All Office Actions for P&G Case 13413CC; U.S. Appl. No. 15/376,691.
All Office Actions for P&G Case 14147; U.S. Appl. No. 14/966,231.
All Office Actions for P&G Case 14600; U.S. Appl. No. 15/358,171.
All Office Actions for P&G Case 14016; U.S. Appl. No. 14/855,653.
All Office Actions for P&G Case 14017; U.S. Appl. No. 14/855,662.
All Office Actions for P&G Case 14018; U.S. Appl. No. 14/855,677.

* cited by examiner

FLUID COMPOSITION AND A MICROFLUIDIC DELIVERY CARTRIDGE COMPRISING THE SAME

FIELD

The present disclosure relates to an improved fluid composition and microfluidic delivery cartridge for dispensing the fluid composition.

BACKGROUND

Recent attempts have been made to deliver fluid compositions, such as fluid compositions comprising a perfume mixture, into the air or onto a substrate using microfluidic delivery systems. Such microfluidic delivery systems may include a microfluidic die having a plurality of nozzles for dispensing the fluid composition. One problem with microfluidic dies is clogging of the nozzles after repeated use of the microfluidic delivery system. Clogging may occur due to impurities in the fluid composition or due to the components of the fluid composition. Once a nozzle(s) clogs, it can be difficult or impossible for a user to clear the blockage. As a result, flow rate out of the microfluidic delivery system may decline over time, resulting in flow rates of fluid composition being dispensed or increased operating times to make up for the lower flow rates. As such, there remains a need for a fluid composition that minimizes clogging of the nozzles of a microfluidic die.

SUMMARY

A. A cartridge comprising a microfluidic die and a fluid composition in fluid communication with the microfluidic die, the fluid composition comprising:
about 50 wt. % to about 100 wt. % of a perfume mixture, by weight of the overall composition, wherein the perfume mixture has a mol-weighted average C log P of less than or equal to about 2.9;
an oxygenated solvent selected from the group consisting of: a polyol, glycol ether, polyether, or combination thereof; and
about 0.25 wt. % to about 9.5 wt. % water, by weight of overall composition.
B. The cartridge of Paragraph A, wherein the mol-weighted average boiling point of the perfume mixture is less than 250° C.
C. The cartridge of Paragraph A or Paragraph B, wherein the perfume mixture has a mol-weighted average C log P of less than or equal to about 2.5.
D. The cartridge of any of Paragraphs A through C comprising about 0.25 wt. % to about 7.0 wt. % water, by weight of the overall composition.
E. The cartridge of any of Paragraphs A through D, wherein the fluid composition is substantially free of suspended solids.
F. The cartridge of any of Paragraphs A through E, wherein the oxygenated solvent is a polyol.
G. The cartridge of Paragraph F, wherein the oxygenated solvent is a glycol ether.
H. The cartridge of any of Paragraphs A through G, wherein the oxygenated solvent is present at a level of about 0.01 wt. % to about 20 wt. %, by weight of the overall composition.
I. The cartridge of any of Paragraphs A through H, wherein the microfluidic die comprises a heater.
J. A method of dispensing a fluid composition from a microfluidic die, the method comprising the steps of:
comprising a housing and a cartridge that is connectable with the housing, wherein the cartridge comprises a reservoir, a fluid transport member, a fluid composition, and a microfluidic die, the fluid composition comprising:
about 50% to about 100%, by weight of the fluid composition, of a perfume mixture, wherein the perfume mixture has an average C log P of less than about 2.9;
an oxygenated solvent selected from the group consisting of: a polyol, glycol ether, polyether, or combination thereof; and
about 0.25 wt. % to about 7 wt. %, by weight of the fluid composition, of water.
K. The method of Paragraph J, wherein the mol-weighted average boiling point of the perfume mixture is less than 250° C.
L. The method of Paragraph J or Paragraph K, wherein the perfume mixture has a mol-weighted average C log P of less than or equal to about 2.5.
M. The method of any of Paragraphs J through L comprising about 0.25 wt. % to about 7.0 wt. % water, by weight of the overall composition.
N. The method of any of Paragraphs J through M, wherein the oxygenated solvent is present at a level of about 0.01 wt. % to about 20 wt. %, by weight of the overall composition.

DETAILED DESCRIPTION

Figure 1:
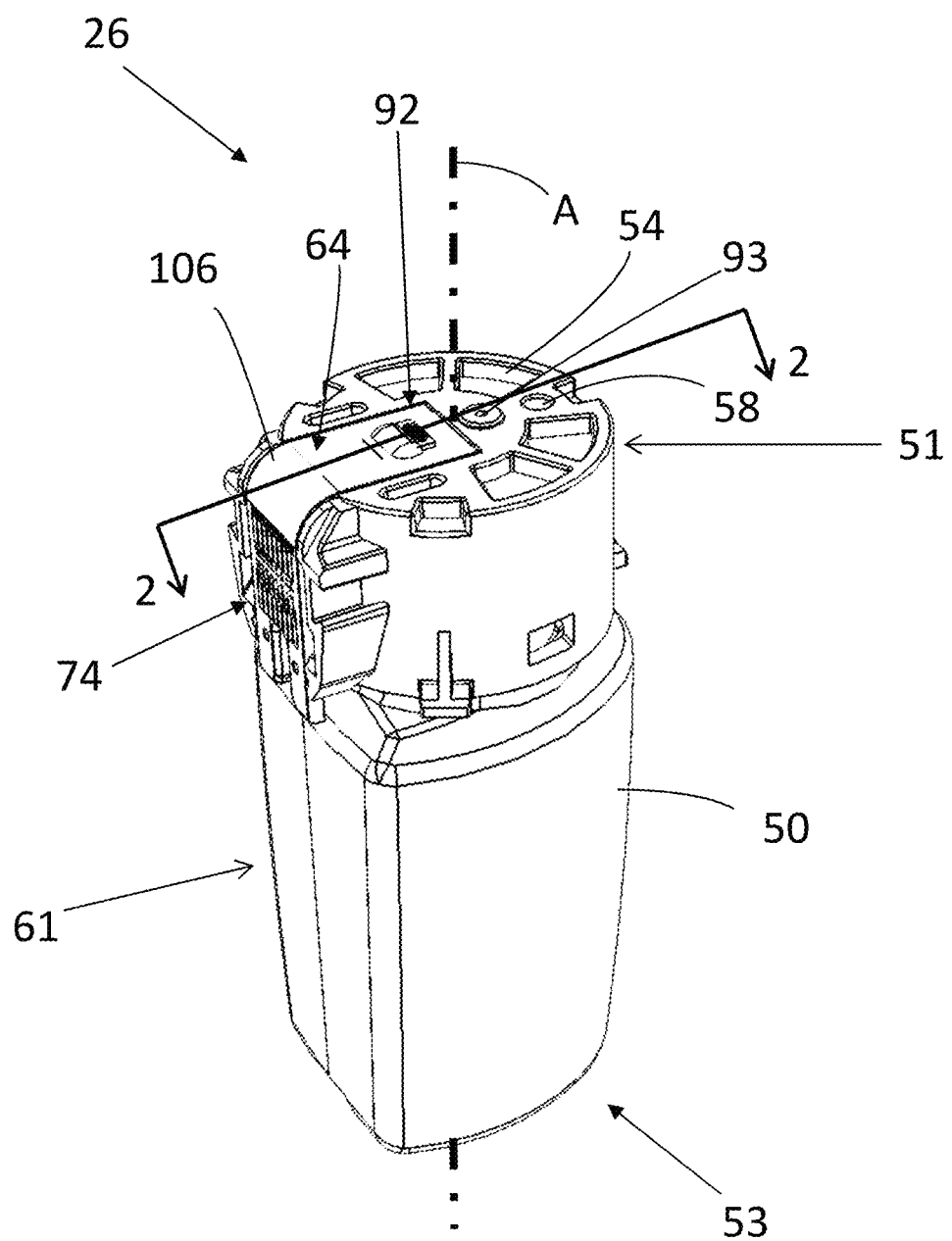
FIG. 1 is a perspective view of a cartridge that includes a reservoir with a microfluidic delivery member and a rigid PCB connected therewith.

The present disclosure is directed to a fluid composition comprising a perfume mixture and water. The fluid composition may also include an oxygenated solvent. The fluid composition of the present disclosure may be used with a cartridge comprising a microfluidic die. The fluid composition may comprise from about 0.25 wt. % to about 9.5 wt. % water, alternatively about 0.25 wt. % to about 7.0 wt. %, by weight of the fluid composition, of water. The fluid composition may comprise at least 50%, or at least 60%, or at least 75%, or at least 85%, by weight of the fluid composition, of a perfume mixture. It has been found that fluid compositions of the present disclosure comprising from about 0.25 wt. % to about 9.5 wt. % water, alternatively about 0.25 wt. % to about 7.0 wt. %, by weight of the fluid composition, in combination with a perfume mixture provides improved dispensing from a microfluidic delivery cartridge. For example, a fluid composition having from about 0.25 wt. % to about 9.5 wt. % water, alternatively about 0.25 wt. % to about 7.0 wt. % water, by weight of the fluid composition, in combination with a perfume mixture results in reduced clogging of the nozzles of the microfluidic die and/or increased flow rates compared to a fluid composition comprising a perfume mixture in the absence of water. It was not expected that water would improve the dispensing of the fluid composition from a microfluidic die because the fluid composition contains a high level of a perfume mixture that is not miscible in water.

The cartridge may comprise a reservoir for containing a fluid composition, a microfluidic delivery member, and a fluid transport member disposed within the reservoir and configured to deliver a fluid composition from within the reservoir to the microfluidic delivery member. The microfluidic delivery member may be configured to dispense the fluid composition into the air.

The cartridge may be connectable with a housing to form a microfluidic delivery system. The cartridge may be fixed with the housing, removeably connectable with the housing, and/or replaceable and may be disposed at least partially within the housing. The cartridge is electrically connectable with the housing.

The microfluidic die may include at least one heater or piezo crystal.

It is to be understood that the cartridge, housing, and microfluidic delivery system are not limited to the construction and arrangement set forth in the following description or illustrated in the drawings. The microfluidic delivery system, cartridge, and housing of the present disclosure are applicable to other configurations or may be practiced or carried out in various ways. For example, the components of the housing may be located on the cartridge and vice-versa. Further, the housing and cartridge may be configured as a single unit versus constructing a cartridge that is separable from the housing as described in the following description. Moreover, the cartridge may be used with various devices for delivering the fluid composition into the air or onto a target surface.

Cartridge

With reference to FIGS. 1 and 2, the cartridge 26 may comprise a reservoir 50 for containing a fluid composition 52. The cartridge 26 may include a die 92 and a fluid transport member 80. The fluid transport member 80 may be configured to deliver fluid composition from the reservoir 50 to the die 92. The die 92 may be configured to dispense the fluid composition into the air or onto a target surface.

Fluid Composition

To operate satisfactorily in a microfluidic delivery system, many characteristics of a fluid composition are taken into consideration. Some factors include formulating fluid compositions with viscosities that are optimal to emit from the microfluidic delivery member, formulating fluid compositions with limited amounts or no suspended solids that would clog the microfluidic delivery member, formulating fluid compositions to be sufficiently stable to not dry and clog the microfluidic delivery member, formulating fluid compositions that are not flammable, etc. For adequate dispensing from a microfluidic die, proper atomization and effective delivery of an air freshening or malodor reducing composition may be considered in designing a fluid composition. It has been found that a fluid composition comprising a perfume mixture, a polyol, and water provides satisfactory atomization and reduced clogging for delivering a freshening or malodor reducing composition into the air. Preferably, the fluid composition comprises from about 50% to about 100%, by weight of the fluid composition, of a perfume mixture, a polyol; and from about 0.25 wt. % to about 9.5 wt. % water, alternatively about 0.25 wt. % to about 7.0 wt. % water, by weight of the fluid composition. Without wishing to be bound by theory, it is believed that the addition of water the fluid composition comprising a perfume mixture reduces the boiling point of the fluid composition, which in turn reduces the energy or heat needed to atomize the fluid composition. As a result of a reduced firing temperature on the heater of the die, it is believed that less fluid composition and less decomposition products of the fluid composition build up on the heater. Moreover, it is believed that water increases the spray rate by dispensing more of the fluid composition in the nozzle at each firing, which results in fewer firings out of each nozzle of the die or a reduced number of required nozzles for the desired spray rate, resulting in an increased life to the nozzles. In order to facilitate incorporation of water, the perfume mixture may have a molar weighted average C log P of less than about 2.9.

The fluid composition may exhibit a viscosity of less than 20 centipoise ("cps"), alternatively less than 18 cps, alternatively less than 16 cps, alternatively from about 5 cps to about 16 cps, alternatively about 8 cps to about 15 cps. And, the fluid composition may have surface tensions below about 35, alternatively from about 20 to about 30 dynes per centimeter. Viscosity is in cps, as determined using a TA Instrument Rheometer: Model AR-G2 (Discovery HR-2) with a single gap stainless steel cup and bob under the following conditions:

Settings:
Temperature 25° C.
Duration 60.0 s
Strain % 2%
Angular frequency 10 rad/s
Geometry: 40 mm parallel Plate (Peltier Plate Steel)
Run Procedure Information:
Conditioning
temperature 25 C
no pre-shear
equilibration 2 minutes Steady State Flow
ramp 1-100 l/s
mode—log
5 points/decade
sample period 10 seconds
5% tolerance with 3 consecutive within tolerance The fluid composition may be substantially free of suspended solids or solid particles existing in a mixture wherein particulate matter is dispersed within a liquid matrix. The fluid composition may have less than 5 wt. % of suspended solids, alternatively less than 4 wt. % of suspended solids, alternatively less than 3 wt. % of suspends, alternatively less than 2 wt. % of suspended solids, alternatively less than 1 wt. % of suspended solids, alternatively less than 0.5 wt. % of suspended solids, or free of suspended solids. Suspended solids are distinguishable from dissolved solids that are characteristic of some perfume materials.

It is contemplated that the fluid composition may comprise other volatile materials in addition to or in substitution for the perfume mixture including, but not limited to, volatile dyes; compositions that function as insecticides; essential oils or materials that acts to condition, modify, or otherwise modify the environment (e.g. to assist with sleep, wake, respiratory health, and like conditions); deodorants or malodor control compositions (e.g. odor neutralizing materials such as reactive aldehydes (as disclosed in U.S. 2005/0124512), odor blocking materials, odor masking materials, or sensory modifying materials such as ionones (also disclosed in U.S. 2005/0124512)).

Perfume Mixture

The fluid composition comprises a perfume mixture present in an amount greater than about 50%, by weight of the fluid composition, alternatively greater than about 60%, alternatively greater than about 70%, alternatively greater than about 75%, alternatively greater than about 80%, alternatively from about 50% to about 100%, alternatively from about 60% to about 100%, alternatively from about 70% to about 100%, alternatively from about 80% to about 100%, alternatively from about 90% to about 100%. The fluid composition may consist entirely of the perfume mixture (i.e. 100 wt. %).

The perfume mixture may contain one or more perfume raw materials. The raw perfume materials are selected based on the material's boiling point ("B.P."). The B.P. referred to herein is the boiling point under normal standard pressure of 760 mm Hg. The B.P. of many perfume ingredients, at standard 760 mm Hg can be found in "Perfume and Flavor Chemicals (Aroma Chemicals)," written and published by Steffen Arctander, 1969. Where the experimentally measured boiling point of individual components is not available, the value may be estimated by the boiling point PhysChem model available from ACD/Labs (Toronto, Ontario, Canada).

The perfume mixture may have a mol-weighted average log of the octanol-water partitioning coefficient ("C log P") of less than about 2.9, alternatively less than about 2.5, alternatively less than about 2.0. Where the experimentally measured log P of individual components is not available, the value may be estimated by the boiling point PhysChem model available from ACD/Labs (Toronto, Ontario, Canada).

The perfume mixture may have a mol-weighted average B.P. of less than 250° C., alternatively less than 225° C., alternatively less than 200° C., alternatively less than about 150° C., or alternatively about 150° C. to about 250° C.

Alternatively, about 3 wt % to about 25 wt % of the perfume mixture may have a mol-weighted average B.P. of less than 200° C., alternatively about 5 wt % to about 25 wt % of the perfume mixture has a mol-weighted average B.P. of less than 200° C.

For purposes of the present disclosure, the perfume mixture boiling point is determined by the mole-weighted average boiling point of the individual perfume raw materials making up said perfume mixture. Where the boiling point of the individual perfume materials is not known from published experimental data, it is determined by the boiling point PhysChem model available from ACD/Labs.

Table 1 lists some non-limiting, exemplary individual perfume materials suitable for the perfume mixture.

TABLE 1

| CAS Number | Perfume Raw Material Name | B.P. (° C.) |
|---|---|---|
| 105-37-3 | Ethyl propionate | 99 |
| 110-19-0 | Isobutyl acetate | 116 |
| 928-96-1 | Beta gamma hexenol | 157 |
| 80-56-8 | Alpha Pinene | 157 |
| 127-91-3 | Beta Pinene | 166 |
| 1708-82-3 | cis-hexenyl acetate | 169 |
| 124-13-0 | Octanal | 170 |
| 40-82-6 | Eucalyptol | 175 |
| 141-78-6 | Ethyl acetate | 77 |

Table 2 shows an exemplary perfume mixture having a total molar weighted average B.P. ("mol-weighted average boiling point") less than 200° C. In calculating the mol-weighted average boiling point, the boiling point of perfume raw materials that may be difficult to determine, may be neglected if they comprise less than 15% by weight of the total perfume mixture, as exemplified in Table 2.

TABLE 2

| CAS Number | Perfume Raw Material Name | Wt % | Molecular Weight | Mol % | B.P. (° C.) |
|---|---|---|---|---|---|
| 123-68-2 | Allyl Caproate | 2.50 | 156.2 | 2.6 | 185 |
| 140-11-4 | Benzyl Acetate | 3.00 | 150.2 | 3.3 | 214 |
| 928-96-1 | Beta Gamma Hexenol | 9.00 | 100.2 | 14.8 | 157 |
| 18479-58-8 | Dihydro Myrcenol | 5.00 | 156.3 | 5.3 | 198 |
| 39255-32-8 | Ethyl 2 Methyl Pentanoate | 9.00 | 144.2 | 10.3 | 157 |
| 77-83-8 | Ethyl Methyl Phenyl Glycidate | 2.00 | 206.2 | 1.6 | 260 |
| 7452-79-1 | Ethyl-2-Methyl Butyrate | 8.00 | 130.2 | 10.1 | 132 |
| 142-92-7 | Hexyl Acetate | 12.50 | 144.2 | 14.3 | 146 |
| 68514-75-0 | Orange Phase Oil 25X1.18%-Low Cit. 14638 | 10.00 | mixture | neglected | 177 |
| 93-58-3 | Methyl Benzoate | 0.50 | 136.1 | 0.6 | 200 |
| 104-93-8 | Para Cresyl Methyl Ether | 0.20 | 122.2 | 0.3 | 176 |

TABLE 2-continued

| CAS Number | Perfume Raw Material Name | Wt % | Molecular Weight | Mol % | B.P. (° C.) |
|---|---|---|---|---|---|
| 1191-16-8 | Prenyl Acetate | 8.00 | 128.2 | 10.3 | 145 |
| 88-41-5 | Verdox | 3.00 | 198.3 | 2.5 | 223 |
| 58430-94-7 | Iso Nonyl Acetate | 27.30 | 186.3 | 24.1 | 225 |
| | TOTAL: | 100.00 | | 100.0 | |
| | Mol-weighted average B.P. | | | | 176.4 |

Water

The fluid composition comprises water. The fluid composition may comprise water in an amount from about 0.25 wt. % to about 9.5 wt. % water, alternatively about 0.25 wt. % to about 7.0 wt. % water, alternatively about 1% to about 5% water, alternatively from about 1% to about 3% water, alternatively from about 1% to about 2% water, by weight of the fluid composition. Without wishing to be bound by theory, it has been found that by formulating the perfume mixture to have a mol-weighted average C log P of less than about 2.5, water can be incorporated into the fluid composition at a level of about 0.25 wt. % to about 9.5 wt. %, alternatively about 0.25 wt. % to about 7.0 wt. %, by weight of the overall composition.

Oxygenated Solvent

The fluid composition may contain one or more oxygenated solvent such as a polyol (components comprising more than one hydroxyl functionality), a glycol ether, or a polyether.

Exemplary oxygenated solvents comprising polyols include ethylene glycol, diethylene glycol, triethylene glycol, propylene glycol, dipropylene glycol, and/or glycerin. The polyol used in the freshening composition of the present invention may be, for example glycerin, ethylene glycol, propylene glycol, dipropylene glycol.

Exemplary oxygenated solvents comprising polyethers are polyethylene glycol, and polypropylene glycol Exemplary oxygenated solvents comprising glycol ethers are propylene glycol methyl ether, propylene glycol phenyl ether, propylene glycol methyl ether acetate, propylene glycol n-butyl ether, dipropylene glycol n-butyl ether, dipropylene glycol n-propyl ether, ethylene glycol phenyl ether, diethylene glycol n-butyl ether, dipropylene glycol n-butyl ether, diethylene glycol mono butyl ether, dipropylene glycol methyl ether, tripropylene glycol methyl ether, tripropylene glycol n-butyl ether, other glycol ethers, or mixtures thereof. The oxygenated solvent may be ethylene glycol, propylene glycol, or mixtures thereof. The glycol used may be diethylene glycol.

The oxygenated solvent may be added to the composition at a level of from about 0.01 wt. % to about 20 wt. %, by weight of the composition, alternatively from about 0.05 wt. % to about 10 wt. %, alternatively from about 0.1 wt. % to about 5 wt. %, by weight of the overall composition.

Functional Perfume Components

The fluid composition may contain functional perfume components ("FPCs"). FPCs are a class of perfume raw materials with evaporation properties that are similar to traditional organic solvents or volatile organic compounds ("VOCs"). "VOCs", as used herein, means volatile organic compounds that have a vapor pressure of greater than 0.2 mm Hg measured at 20° C. and aid in perfume evaporation. Exemplary VOCs include the following organic solvents: dipropylene glycol methyl ether ("DPM"), 3-methoxy-3-methyl-1-butanol ("MMB"), volatile silicone oil, and dipropylene glycol esters of methyl, ethyl, propyl, butyl, ethylene glycol methyl ether, ethylene glycol ethyl ether, diethylene glycol methyl ether, diethylene glycol ethyl ether, or any VOC under the tradename of Dowanol™ glycol ether. VOCs are commonly used at levels greater than 20% in a fluid composition to aid in perfume evaporation.

The FPCs aid in the evaporation of perfume materials and may provide a hedonic, fragrance benefit. FPCs may be used in relatively large concentrations without negatively impacting perfume character of the overall composition. As such, the fluid composition may be substantially free of VOCs, meaning it has no more than 18%, alternatively no more than 6%, alternatively no more than 5%, alternatively no more than 1%, alternatively no more than 0.5%, by weight of the composition, of VOCs. The fluid composition may be free of VOCs.

Perfume materials that are suitable as a FPC may have a KI, as defined above, from about 800 to about 1500, alternatively about 900 to about 1200, alternatively about 1000 to about 1100, alternatively about 1000.

Perfume materials that are suitable for use as a FPC can also be defined using odor detection threshold ("ODT") and non-polarizing scent character for a given perfume character scent camp. ODTs may be determined using a commercial GC equipped with flame ionization and a sniff-port. The GC is calibrated to determine the exact volume of material injected by the syringe, the precise split ratio, and the hydrocarbon response using a hydrocarbon standard of known concentration and chain-length distribution. The air flow rate is accurately measured and, assuming the duration of a human inhalation to last 12 seconds, the sampled volume is calculated. Since the precise concentration at the detector at any point in time is known, the mass per volume inhaled is known and concentration of the material can be calculated. To determine whether a material has a threshold below 50 ppb, solutions are delivered to the sniff port at the back-calculated concentration. A panelist sniffs the GC effluent and identifies the retention time when odor is noticed. The average across all panelists determines the threshold of noticeability. The necessary amount of analyte is injected onto the column to achieve a 50 ppb concentration at the detector. Typical GC parameters for determining ODTs are listed below. The test is conducted according to the guidelines associated with the equipment.

Equipment:
  GC: 5890 Series with FID detector (Agilent Technologies, Ind., Palo Alto, Calif., USA);
  7673 Autosampler (Agilent Technologies, Ind., Palo Alto, Calif., USA);
  Column: DB-1 (Agilent Technologies, Ind., Palo Alto, Calif., USA)
  Length 30 meters ID 0.25 mm film thickness 1 micron (a polymer layer on the inner wall of the capillary tubing, which provide selective partitioning for separations to occur).

Method Parameters:
Split Injection: 17/1 split ratio;
Autosampler: 1.13 microliters per injection;
Column Flow: 1.10 mL/minute;
Air Flow: 345 mL/minute;
Inlet Temp. 245° C.;
Detector Temp. 285° C.
Temperature Information:
Initial Temperature: 50° C.;
Rate: 5 C/minute;
Final Temperature: 280° C.;
Final Time: 6 minutes;
Leading assumptions: (i) 12 seconds per sniff
   (ii) GC air adds to sample dilution.

FPCs may have an ODT from greater than about 1.0 parts per billion ("ppb"), alternatively greater than about 5.0 ppb, alternatively greater than about 10.0 ppb, alternatively greater than about 20.0 ppb, alternatively greater than about 30.0 ppb, alternatively greater than about 0.1 parts per million.

The FPCs in a fluid composition may have a KI in the range from about 900 to about 1400; alternatively from about 1000 to about 1300. These FPCs can be either an ether, an alcohol, an aldehyde, an acetate, a ketone, or mixtures thereof.

FPCs may be volatile, low B.P. perfume materials. Exemplary FPC include iso-nonyl acetate, dihydro myrcenol (3-methylene-7-methyl octan-7-ol), linalool (3-hydroxy-3, 7-dimethyl-1,6 octadiene), geraniol (3,7 dimethyl-2,6-octadien-1-ol), d-limonene (1-methyl-4-isopropenyl-1-cyclohexene, benzyl acetate, isopropyl mystristate, and mixtures thereof. Table 3 lists the approximate reported values for exemplary properties of certain FPCs.

TABLE 3

| FPC | B.P. (° C.) | MW | Clog P @ 25° C. | Flash point (° C.) | Vapor pressure | KI | ODT |
|---|---|---|---|---|---|---|---|
| Iso-Nonyl Acetate (CAS# 58430-94-7) | 225 | 186.3 | 4.28 | 79.4 | 0.11 | 1178 | 12 ppb |
| Dihydro Myrcenol (CAS# 18479-58-8) | 198 | 156.3 | 3.03 | 76.1 | 0.1 | 1071 | 32 ppb |
| Linalool (CAS# 78-70-6) | 205 | 154.3 | 2.549 | 78.9 | 0.05 | 1107 | 22 ppb |
| Geraniol (CAS# 106-24-1) | 237 | 154.3 | 2.769 | 100 | 0.00519 | 1253 | 0.4 ppb |
| D-Limonene (CAS# 94266-47-4) | 170 | 136 | 4.35 | 47.2 | 1.86 | 1034 | 204 ppb |

The total amount of FPCs in the perfume mixture may be greater than about 50%, alternatively greater than about 60%, alternatively greater than about 70%, alternatively greater than about 75%, alternatively greater than about 80%, alternatively from about 50% to about 100%, alternatively from about 60% to about 100%, alternatively from about 70% to about 100%, alternatively from about 75% to about 100%, alternatively from about 80% to about 100%, alternatively from about 85% to about 100%, alternatively from about 90% to about 100%, alternatively about 100%, by weight of the perfume mixture. The perfume mixture may consist entirely of FPCs (i.e. 100 wt. %).

Table 4 lists a non-limiting, exemplary fluid composition comprising FPCs and their approximate reported values for KI and B.P.

TABLE 4

| Material Name | KI | wt. % | B.P. (° C.) |
|---|---|---|---|
| Benzyl Acetate (CAS # 140-11-4) | 1173 | 1.5 | 214 |
| Ethyl-2-methyl Butyrate (CAS # 7452-79-1) | 850 | 0.3 | 132 |
| Amyl Acetate (CAS # 628-63-7) | 912 | 1.0 | 149 |
| Cis 3 Hexenyl Acetate (CAS # 3681-71-8) | 1009 | 0.5 | 169 |
| Ligustral (CAS # 27939-60-2) | 1094 | 0.5 | 177 |
| Melonal (CAS # 106-72-9) | 1060 | 0.5 | 116 |
| Hexyl Acetate (CAS # 142-92-7) | 1016 | 2.5 | 146 |
| Dihydro Myrcenol (CAS# 18479-58-8) | 1071 | 15 | 198 |
| Phenyl Ethyl Alcohol (CAS# 60-12-8) | 1122 | 8 | 219 |
| Linalool (CAS # 78-70-6) | 1243 | 25.2 | 205 |
| Geraniol (CAS# 106-24-1) | 1253 | 5 | 238 |
| Iso Nonyl Acetate (CAS# 40379-24-6) | 1295 | 22.5 | 225 |
| Benzyl Salicylate (CAS # 118-58-1) | 2139 | 3 | 320 |
| Coumarin (CAS # 91-64-5) | 1463 | 1.5 | 267 |
| Methyl Dihydro Jasmonate (CAS# 24851-98-7) | 1668 | 7 | 314 |
| Hexyl Cinnamic Aldehyde (CAS # 101-86-0) | 1770 | 6 | 305 |

When formulating fluid compositions, one may also include solvents, diluents, extenders, fixatives, thickeners, or the like. Non-limiting examples of these materials are ethyl alcohol, carbitol, diethylene glycol, dipropylene glycol, diethyl phthalate, triethyl citrate, isopropyl myristate, ethyl cellulose, and benzyl benzoate.

Reservoir

Figure 2:
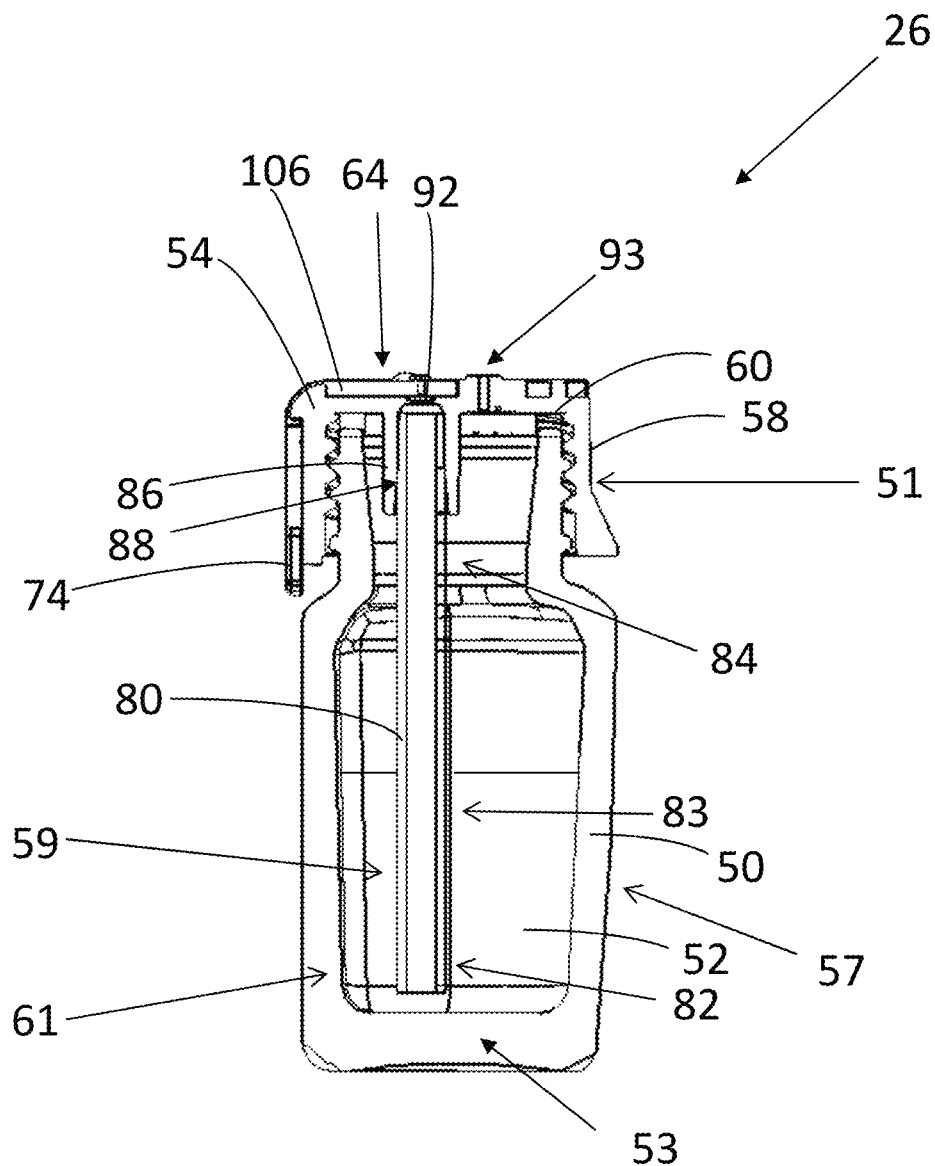
FIG. 2 is a sectional view of FIG. 1 taken along line 2-2.

With reference to FIGS. 1 and 2, the cartridge 26 includes a reservoir 50 for containing a fluid composition. The reservoir 50 may be configured to contain from about 5 milliliters (mL) to about 100 mL, alternatively from about 10 mL to about 50 mL, alternatively from about 15 mL to about 30 mL of fluid composition. The cartridge 26 may be configured to have multiple reservoirs, with each reservoir containing the same or a different fluid composition. The reservoir can be made of any suitable material for containing a fluid composition including glass, plastic, metal, or the like.

The reservoir 50 may be comprised of a top portion 51, a base portion 53 opposing the top portion 51, and at least one sidewall 61 connected with and extending between the top portion 51 and the base portion 53. The reservoir 50 may define an interior 59 and an exterior 57. The reservoir 50 may include an air vent 93. While the reservoir 50 is shown as having a top portion 51, a base portion 53, and at least one sidewall 61, it is to be appreciated that the reservoir 50 may be configured in various different ways.

The reservoir 50, including the top portion 51, base portion 53, and sidewall(s) 61, may be configured as a single element or may be configured as separate elements that are joined together. For example, the top portion 51 or base portion 53 may be configured as a separate element from the remainder of the reservoir 50. For example, the reservoir 50 may be comprised of two elements joined together; the base portion 53 and the sidewall(s) 61 may be one element and the top portion 51 may be a separate element. The top portion 51 may be configured as a lid 54 that is mechanically connected with the sidewall(s) 61. The lid 54 may be removably or fixably connected with the sidewall(s) 61 to substantially enclose the reservoir 50. The lid 54 may be threadingly attached with the sidewall(s) 61 of the reservoir 50, or may be welded, glued, or the like with the sidewall(s) 61 of the reservoir 50.

With reference to FIG. 2, the reservoir 50 may include a connection member 86 extending from the interior 59 of the reservoir 50. The connection member 86 may define a chamber 88 for receiving a portion of the second end portion 84 of the fluid transport member 80. The chamber 88 may be substantially sealed between the connection member 86 and the fluid transport member 80 to prevent air from the reservoir 50 from entering the chamber 88.

In an example configuration wherein the top portion 51 of the reservoir 50 includes a lid 54, the connection member 86 may extend from the lid 54. The lid 54 of the reservoir may be defined by an outer surface 58 and an inner surface 60. The lid 54 may include a connection member 86 extending from the inner surface 60.

The reservoir may be transparent, translucent, or opaque or any combination thereof. For example, the reservoir may be opaque with a transparent indicator of the level of fluid composition in the reservoir.

Figure 3:
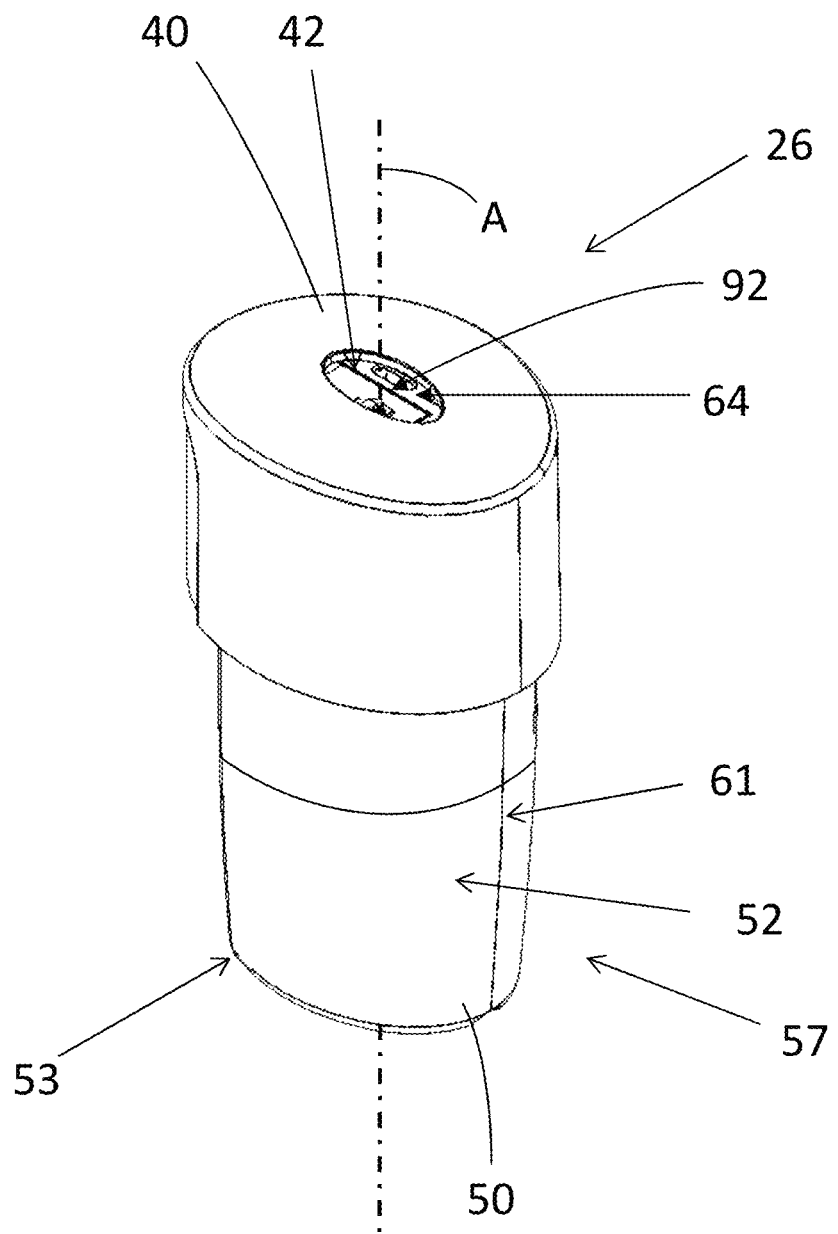
FIG. 3 is a perspective of a cartridge having an outer cap.
Figure 4:
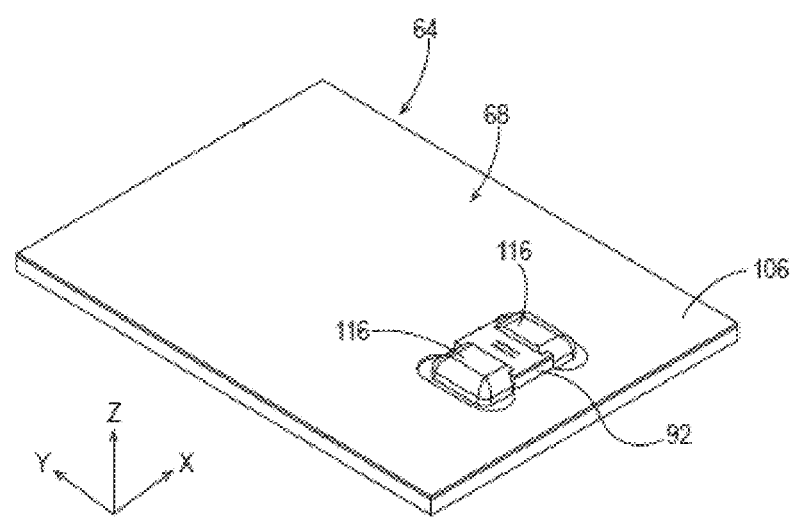
FIG. 4 is a top, perspective view of a microfluidic delivery member having a rigid PCB.
Figure 5:
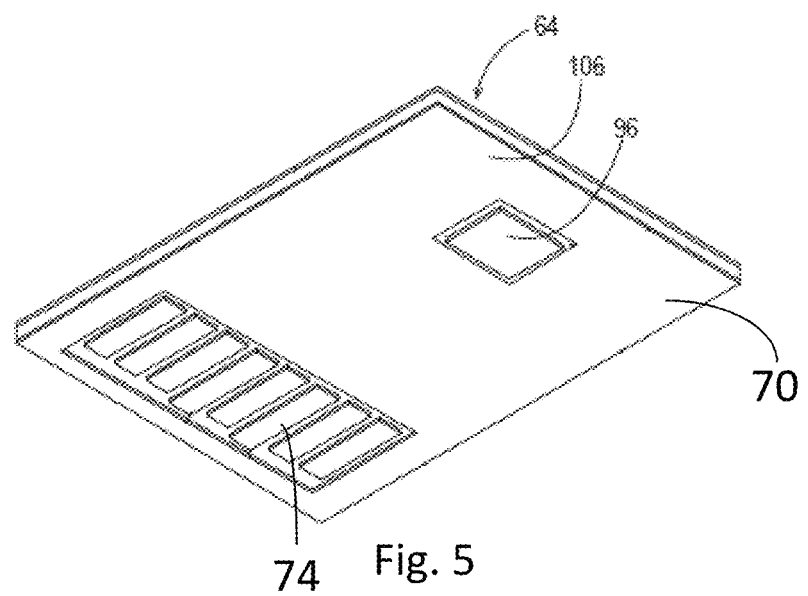
FIG. 5 is a bottom, perspective view of a microfluidic delivery member having a rigid PCB.

As shown in FIG. 3, the cartridge 26 may include an outer cover 40 that is mechanically connected with the reservoir 50. The outer cover 40 may include an orifice 42 that at least partially exposes the die 92. The orifice 42 may be adjacent to the die 92, and may be at least partially aligned with the die 92. An air flow path may be formed in a gap between the reservoir 50 and the outer cover 40. When an outer cover 40 is present, air pressure generated by the fan causes air to travel through the air flow path and out of the orifice 42; the fluid composition 52 dispensed from the die 92 combines with the air exiting the orifice 42, helping the fluid composition 52 to be dispensed into the air and adequately fill a room or space.

Fluid Transport Member

The cartridge 26 may include a fluid transport member 80 disposed within the interior 59 of the reservoir 50. The fluid transport member 80 may be defined by a first end portion 82, a second end portion 84, and a central portion 83. The first end portion 82 is in fluid communication with the fluid composition 52 in the reservoir 50 and the second end portion 84 is operatively connected with the connection member 86 of the reservoir 50. The second end 84 of the fluid transport member 80 is located below the microfluidic delivery member 64. The fluid transport member 80 delivers fluid composition from the reservoir 50 to the microfluidic delivery member 64. Fluid composition can travel by wicking, diffusion, suction, siphon, vacuum, or other mechanism against the force of gravity. The fluid composition may be transported to the microfluidic delivery member 64 by a gravity fed system known in the art.

The fluid transport member 80 may be configured in various ways, including in the form of a capillary tube or wicking material. The wicking material may be in the form of a metal or fabric mesh, sponge, or fibrous or porous wick that contains multiple interconnected open cells that form capillary passages to draw a fluid composition up from the reservoir to the microfluidic delivery member. Non-limiting examples of suitable compositions for the fluid transport member include polyethylene, ultra-high molecular weight polyethelene, nylon 6, polypropylene, polyester fibers, ethyl vinyl acetate, polyether sulfone, polyvinylidene fluoride, and polyethersulfone, polytetrafluroethylene, and combinations thereof. Many traditional ink jet cartridges use an open-cell polyurethane foam which can be incompatible with perfume mixtures over time (e.g. after 2 or 3 months) and can break down. The fluid transport member 80 may be free of a polyurethane foam.

The fluid transport member 80 may be a high density wick composition to aid in containing the scent of a perfume mixture. The fluid transport member may be made from a plastic material chosen from high-density polyethylene or polyester fiber. As used herein, high density wick compositions include any conventional wick material having a pore radius or equivalent pore radius (e.g. in the case of fiber based wicks) ranging from about 20 microns to about 200 microns, alternatively from about 30 microns to about 150 microns, alternatively from about 30 microns to about 125 microns, alternatively, about 40 microns to about 100 microns.

Regardless of the material of manufacture, where a wicking material is used, the fluid transport member 80 can exhibit an average pore size from about 10 microns to about 500 microns, alternatively from about 50 microns to about 150 microns, alternatively about 70 microns. The average pore volume of the wick, expressed as a fraction of the fluid transport member not occupied by the structural composition, is from about 15% to about 85%, alternatively from about 25% to about 50%. Good results have been obtained with wicks having an average pore volume of about 38%.

The fluid transport member 80 may be any shape that is able to deliver fluid composition from the reservoir 50 to the microfluidic delivery member 64. Although the fluid transport member 80 has a width dimension, such as diameter, that is significantly smaller than the reservoir 50, it is to be appreciated that the diameter of the fluid transport member 80 may be larger and may substantially fill the reservoir 50. The fluid transport member 80 can also be of variable length, such as, from about 1 mm to about 100 mm, or from about 5 mm to about 75 mm, or from about 10 mm to about 50 mm.

Microfluidic Delivery Member

The cartridge 26 may comprise a microfluidic delivery member 64 that utilizes aspects of drop-on-demand ink-jet print head systems, and more particularly, aspects of thermal or piezo ink-jet print heads. The microfluidic delivery member 64 may be connected with the top portion 51 and/or sidewall 61 of the reservoir 50 of the cartridge 26.

In a "drop-on-demand" ink-jet printing process, a fluid composition is ejected through a very small orifice of a diameter typically about 5-50 microns, or between about 10 and about 40 microns, in the form of minute droplets by rapid pressure impulses. The rapid pressure impulses are typically generated in the print head by either expansion of a piezoelectric crystal vibrating at a high frequency or volatilization of a volatile composition (e.g. solvent, water, propellant) within the ink by rapid heating cycles. Thermal ink-jet printers employ a heating element within the print head to volatilize a portion of the composition that propels a second portion of fluid composition through the orifice nozzle to form droplets in proportion to the number of on/off cycles for the heating element. The fluid composition is forced out of the nozzle when needed. Conventional ink-jet printers are more particularly described in U.S. Pat. Nos. 3,465,350 and 3,465,351.

The microfluidic delivery member 64 may be in electrical communication with a power source and may include a printed circuit board ("PCB") 106 and a die 92 that is in fluid communication with the fluid transport member 80.

The PCB 106 may be a rigid planar circuit board; a flexible PCB; or a semi-flex PCB. The semi-flex PCB may include a fiberglass-epoxy composite that is partially milled in a portion that allows a portion of the PCB 106 to bend. The PCB 106 may be of a conventional construction. It may comprise a ceramic substrate. It may comprise a fiberglass-epoxy composite substrate material and layers of conductive metal, normally copper, on the top and bottom surfaces. The conductive layers are arranged into conductive paths through an etching process. The conductive paths are protected from mechanical damage and other environmental effects in most areas of the board by a photo-curable polymer layer, often referred to as a soldermask layer. In selected areas, such as the liquid flow paths and wire bond attachment pads, the conductive copper paths are protected by an inert metal layer such as gold. Other material choices could be tin, silver, or other low reactivity, high conductivity metals.

The PCB 106 may include all electrical connections—the contacts 74, the traces 75, and the contact pads 112. The contacts 74 and contact pads 112 may be disposed on the same side of the PCB 106, or may be disposed on different sides of the PCB.

Figure 6:
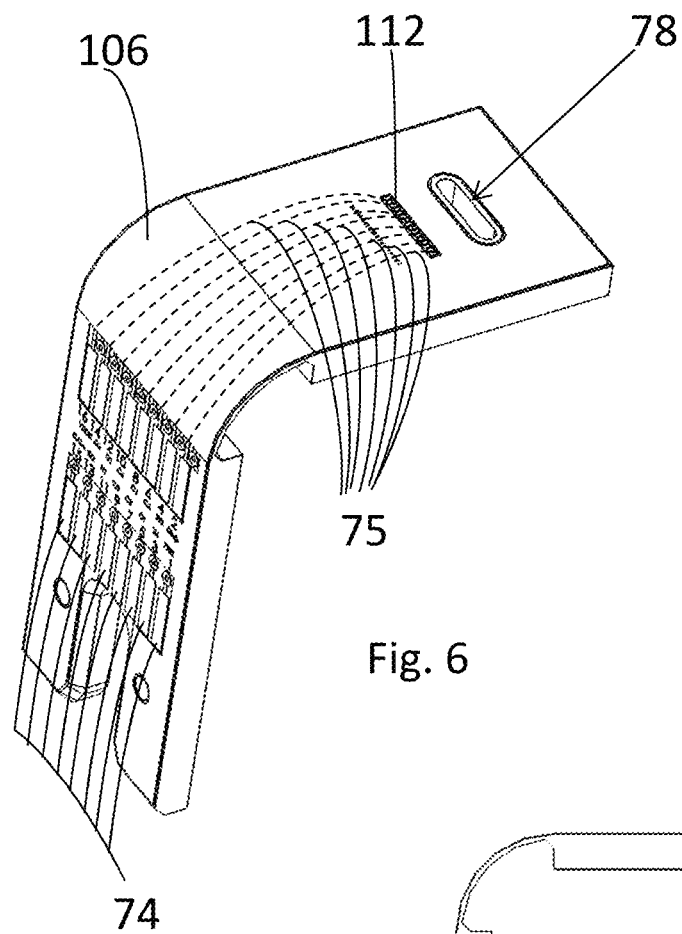
FIG. 6 is a perspective view of a semi-flex PCB for a microfluidic delivery member.
Figure 7:
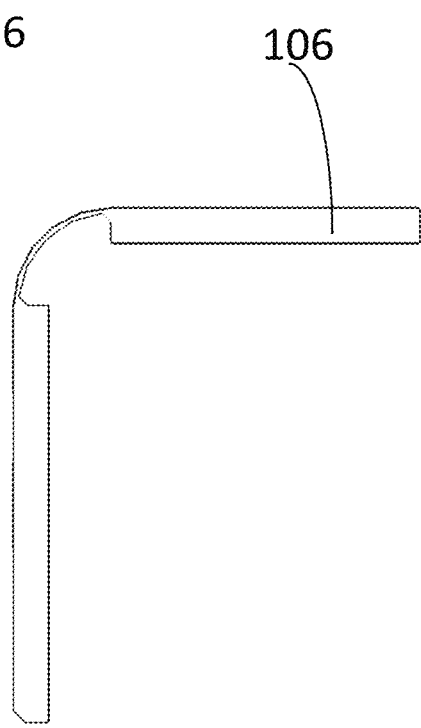
FIG. 7 is a side, elevation view of a semi-flex PCB for a microfluidic delivery member.
Figure 8:
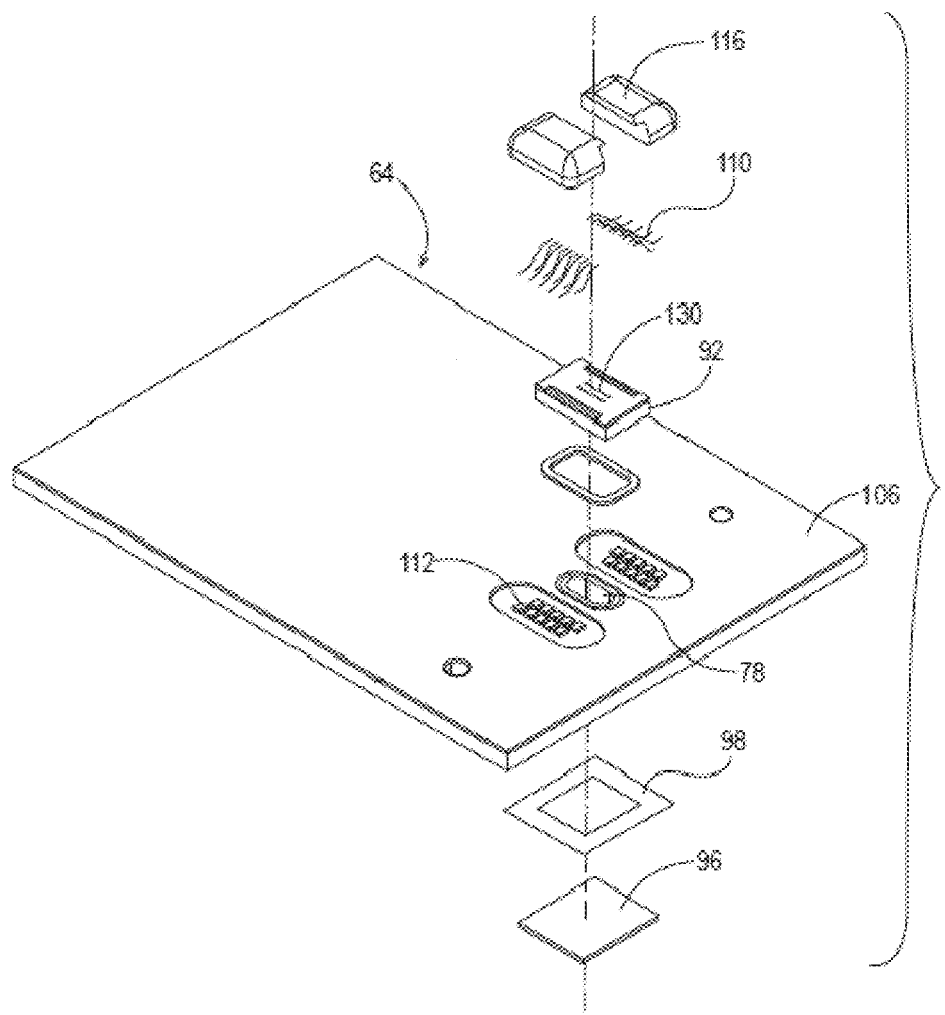
FIG. 8 is an exploded view of a microfluidic delivery member.

With reference to FIGS. 4-9, the PCB 106 includes the electrical contacts 74 at the first end and contact pads 112 at the second end proximate the die 92. With reference to FIG. 6, electrical traces 75 from the contact pads 112 to the electrical contacts are formed on the board and may be covered by the solder mask or another dielectric. Electrical connections from the die 92 to the PCB 106 may be established by a wire bonding process, where small wires, which may be composed of gold or aluminum, are thermally attached to bond pads on the silicon die and to corresponding bond pads on the board. An encapsulant material 116, normally an epoxy compound, is applied to the wire bond area to protect the delicate connections from mechanical damage and other environmental effects.

The PCB 106 may carry a die 92. The die 92 comprises a fluid injection system made by using a semiconductor micro fabrication process such as thin-film deposition, passivation, etching, spinning, sputtering, masking, epitaxy growth, wafer/wafer bonding, micro thin-film lamination, curing, dicing, etc. These processes are known in the art to make MEMs devices. The die 92 may be made from silicon, glass, or a mixture thereof. The die 92 comprises a plurality of microfluidic chambers, each comprising a corresponding actuation element: heating element or electromechanical actuator. In this way, the die's fluid injection system may be micro thermal nucleation (e.g. heating element) or micro mechanical actuation (e.g. thin-film piezoelectric). One type of die for the microfluidic delivery member is an integrated membrane of nozzles obtained via MEMs technology as described in U.S. 2010/0154790, assigned to STMicroelectronics S.R.I., Geneva, Switzerland. In the case of a thin-film piezo, the piezoelectric material (e.g. lead zirconinum titanate)" is typically applied via spinning and/or sputtering processes. The semiconductor micro fabrication process allows one to simultaneously make one or thousands of MEMS devices in one batch process (a batch process comprises of multiple mask layers).

The die 92 may be secured to the upper surface 68 of the PCB 106 above the opening 78. The die 92 may be secured to the upper surface of the PCB 106 by any adhesive material configured to hold the semiconductor die to the board. The adhesive material may be the same or different from the adhesive material used to secure a filter 96 to the microfluidic delivery member 64.

The die 92 may comprise a silicon substrate, conductive layers, and polymer layers. The silicon substrate forms the supporting structure for the other layers, and contains a channel for delivering fluid composition from the bottom of the die to the upper layers. The conductive layers are deposited on the silicon substrate, forming electrical traces with high conductivity and heaters with lower conductivity. The polymer layers form passages, chambers, and nozzles 130 which define the drop formation geometry. The die 92 includes a plurality of electrical connection leads 110 that extend from one of the intermediate layers 109 down to the contact pads 112 on the circuit PCB 106.

The filter 96 may be attached to the PCB with an adhesive material that is not readily degraded by the fluid composition in the reservoir 50. The adhesive may be thermally or ultraviolet activated. The filter 96 is positioned between the chamber 88 and the die 92. The filter 96 is separated from the bottom surface of the microfluidic delivery member 64 by a mechanical spacer 98. The mechanical spacer 98 creates a gap between the bottom surface 70 of the microfluidic delivery member 64 and the filter 96 proximate the opening 78.

FIGS. 9-12 include more details of the die 92. The die 92 includes a substrate 107, a plurality of intermediate layers 109, and a nozzle plate 132. The nozzle plate 132 includes an outer surface 133 that subtends a surface area. The plurality of intermediate layers 109 include dielectric layers and a chamber layer 148 that are positioned between the substrate and the nozzle plate 132. The nozzle plate 132 may be about 12 microns thick.

The die 92 includes a plurality of electrical connection leads 110 that extend from one of the intermediate layers 109 down to the contact pads 112 on the circuit PCB 106. At least one lead couples to a single contact pad 112. Openings 150 on the left and right side of the die 92 provide access to the intermediate layers 109 to which the leads 110 are coupled. The openings 150 pass through the nozzle plate 132 and chamber layer 148 to expose contact pads 152 that are formed on the intermediate dielectric layers. There may be one opening 150 positioned on only one side of the die 92 such that all of the leads that extend from the die extend from one side while other side remains unencumbered by the leads.

Figure 10:
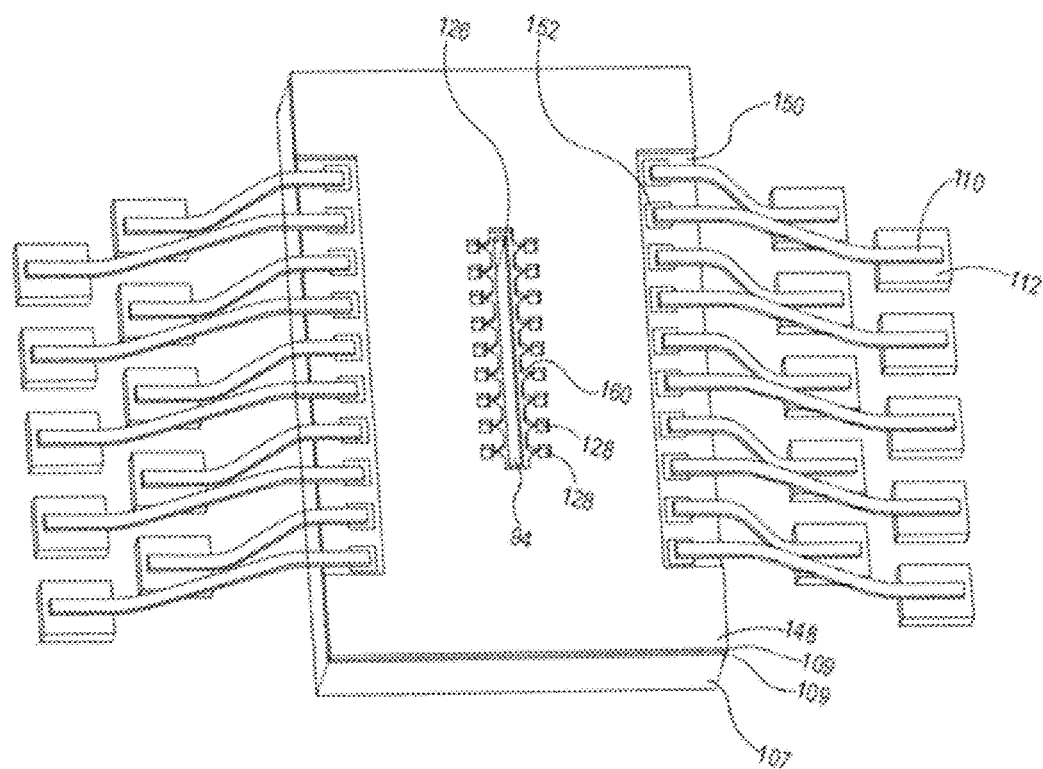
FIG. 10 is a top, perspective view of a die with a nozzle plate removed to show fluid chambers of the die.

The nozzle plate 132 may include about 4-100 nozzles 130, or about 6-80 nozzles, or about 8-64 nozzles. For illustrative purposes only, there are eighteen nozzles 130 shown through the nozzle plate 132, nine nozzles on each side of a center line. Each nozzle 130 may deliver about 0.5 to about 20 picoliters, or about 1 to about 10 picoliters, or about 2 to about 6 picoliters of a fluid composition per electrical firing pulse. The volume of fluid composition delivered from each nozzle per electrical firing pulse may be analyzed using image-based drop analysis where strobe illumination is coordinated in time with the production of drops, one example of which is the JetXpert system, available from ImageXpert, INc. of Nashua, N.H., with the droplets measured at a distance of 1-3 mm from the top of the die. The nozzles 130 may be positioned about 60 um to about 110 µm apart. Twenty nozzles 130 may be present in a 3 mm$^2$ area. The nozzles 130 may have a diameter of about 5 µm to about 40 µm, or 10 µm to about 30 µm, or about 20 µm to about 30 µm, or about 13 µm to about 25 µm. FIG. 10 is a top down isometric view of the die 92 with the nozzle plate 132 removed, such that the chamber layer 148 is exposed.

Figure 12:
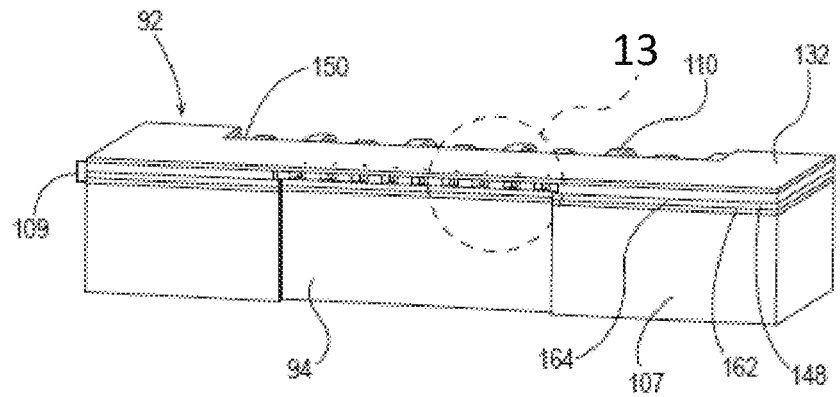
FIG. 12 is a sectional view of FIG. 9 taken along line 12-12.
Figure 13:
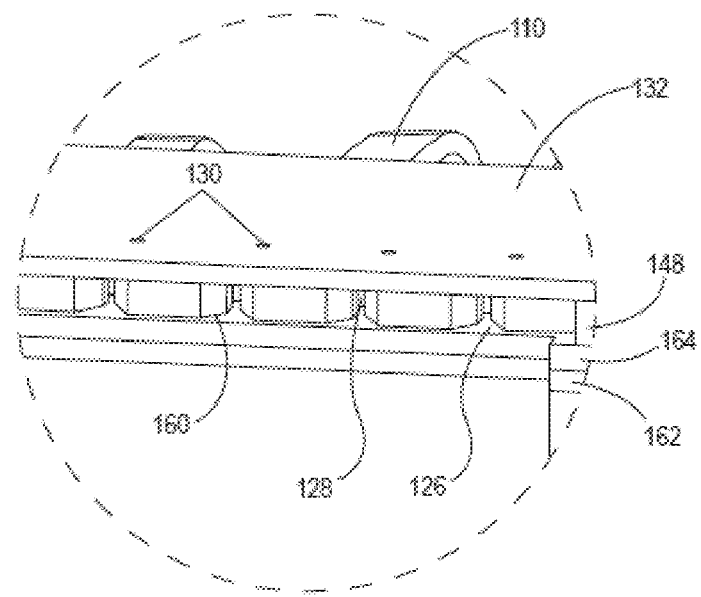
FIG. 13 is an enlarged view of portion 13 taken from FIG. 12.
Figure 14:
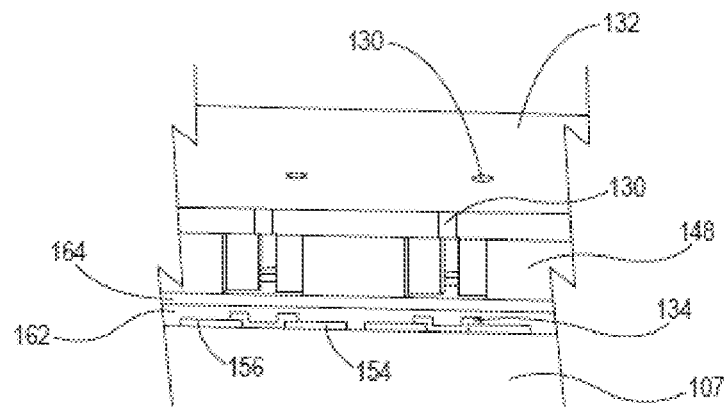
FIG. 14 is a sectional view of FIG. 9 taken along line 14-14.

Generally, the nozzles 130 are positioned along a fluidic feed channel through the die 92 as shown in FIGS. 12 and 13. The nozzles 130 may include tapered sidewalls such that an upper opening is smaller than a lower opening. The heater may be square, having sides with a length. In one example, the upper diameter is about 13 μm to about 18 μm and the lower diameter is about 15 μm to about 20 μm. At 13 μm for the upper diameter and 18 μm for the lower diameter, this would provide an upper area of 132.67 μm and a lower area of 176.63 μm. The ratio of the lower diameter to the upper diameter would be around 1.3 to 1. In addition, the area of the heater to an area of the upper opening would be high, such as greater than 5 to 1 or greater than 14 to 1.

Each nozzle 130 is in fluid communication with the fluid composition in the reservoir 50 by a fluid path. Referring to FIGS. 2 and 8-15 the fluid path from the reservoir 50 includes the first end 82 of the fluid transport member 80, through the transport member to the second end 84 of the transport member, through the chamber 88, through the first through-hole 90, through the opening 78 of the PCB 106, through an inlet 94 of the die 92, then through a channel 126, and then through the chamber 128, and out of the nozzle 130 of the die.

Figure 11:
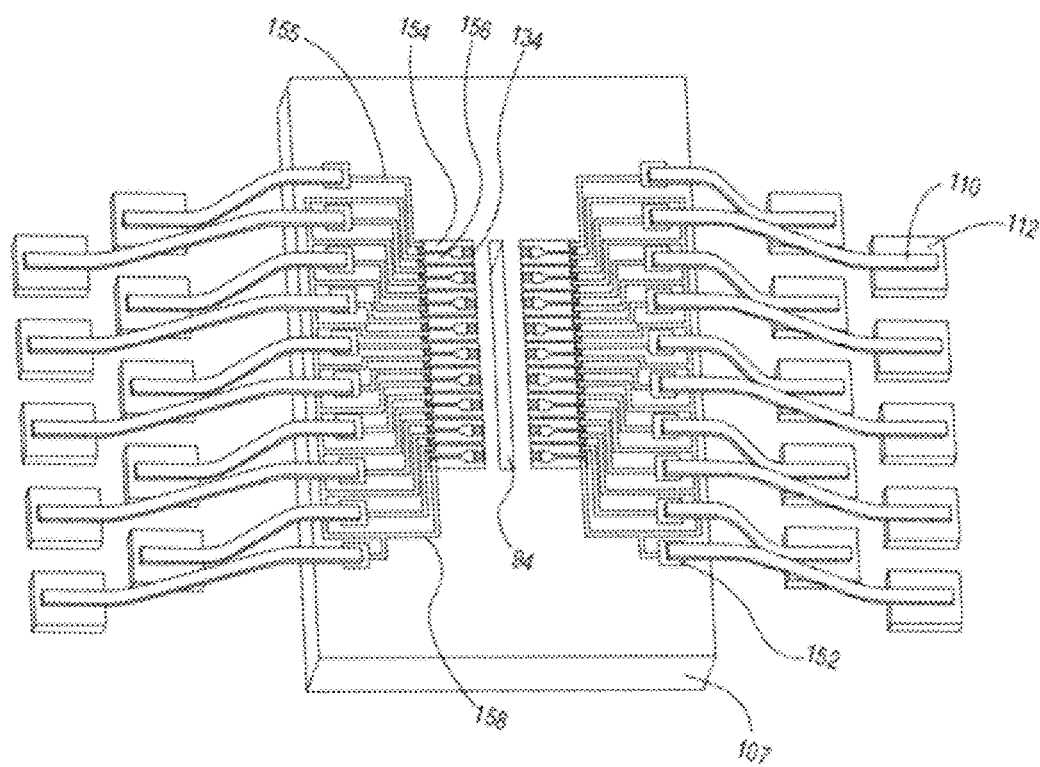
FIG. 11 is a top, perspective view of a die with layers of the die removed to show the dielectric layer of the die.

Proximate each nozzle chamber 128 is a heating element 134 (see FIGS. 11 and 14) that is electrically coupled to and activated by an electrical signal being provided by one of the contact pads 152 of the die 92. Referring to FIG. 11, each heating element 134 is coupled to a first contact 154 and a second contact 156. The first contact 154 is coupled to a respective one of the contact pads 152 on the die by a conductive trace 155. The second contact 156 is coupled to a ground line 158 that is shared with each of the second contacts 156 on one side of the die. There may be only a single ground line that is shared by contacts on both sides of the die. Although FIG. 11 is illustrated as though all of the features are on a single layer, they may be formed on several stacked layers of dielectric and conductive material. Further, while the illustrated embodiment shows a heating element 134 as the activation element, the die 92 may comprise piezoelectric actuators in each chamber 128 to dispense the fluid composition from the die.

In use, when the fluid composition in each of the chambers 128 is heated by the heating element 134, the fluid composition vaporizes to create a bubble. The expansion that creates the bubble causes fluid composition to eject from the nozzle 130 and to form a plume of one or more droplets.

Figure 9:
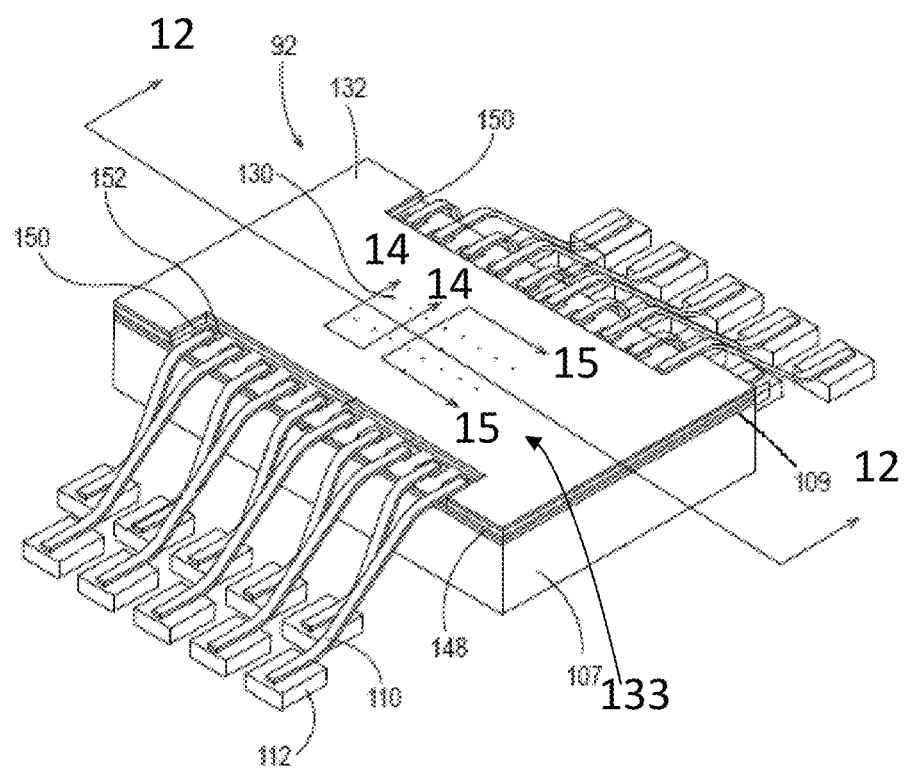
FIG. 9 is a top, perspective view of a die of a microfluidic delivery member.

With reference to FIGS. 9 and 10, the substrate 107 includes an inlet path 94 coupled to a channel 126 that is in fluid communication with individual chambers 128, forming part of the fluid path. Above the chambers 128 is the nozzle plate 132 that includes the plurality of nozzles 130. Each nozzle 130 is above a respective one of the chambers 128. The die 92 may have any number of chambers and nozzles, including one chamber and nozzle. For illustrative purposes only, the die is shown as including eighteen chambers each associated with a respective nozzle. Alternatively, it can have ten nozzles and two chambers provided fluid composition for a group of five nozzles. It is not necessary to have a one-to-one correspondence between the chambers and nozzles.

As best seen in FIG. 10, the chamber layer 148 defines angled funnel paths 160 that feed the fluid composition from the channel 126 into the chamber 128. The chamber layer 148 is positioned on top of the intermediate layers 109. The chamber layer defines the boundaries of the channels and the plurality of chambers 128 associated with each nozzle 130. The chamber layer may be formed separately in a mold and then attached to the substrate. The chamber layer may be formed by depositing, masking, and etching layers on top of the substrate.

The intermediate layers 109 include a first dielectric layer 162 and a second dielectric layer 164. The first and second dielectric layers are between the nozzle plate and the substrate. The first dielectric layer 162 covers the plurality of first and second contacts 154, 156 formed on the substrate and covers the heaters 134 associated with each chamber. The second dielectric layer 164 covers the conductive traces 155.

With reference to FIG. 11, the first and second contacts 154, 156 are formed on the substrate 107. The heaters 134 are formed to overlap with the first and second contacts 154, 156 of a respective heater assembly. The contacts 154, 156 may be formed of a first metal layer or other conductive material. The heaters 134 may be formed of a second metal layer or other conductive material. The heaters 134 are thin-film resistors that laterally connect the first and second contacts 154, 156. Instead of being formed directly on a top surface of the contacts, the heaters 134 may be coupled to the contacts 154, 156 through vias or may be formed below the contacts.

The heater 134 may be a 20-nanometer thick tantalum aluminum layer. The heater 134 may include chromium silicon films, each having different percentages of chromium and silicon and each being 10 nanometers thick. Other materials for the heaters 134 may include tantalum silicon nitride and tungsten silicon nitride. The heaters 134 may also include a 30-nanometer cap of silicon nitride. The heaters 134 may be formed by depositing multiple thin-film layers in succession. A stack of thin-film layers combine the elementary properties of the individual layers.

A ratio of an area of the heater 134 to an area of the nozzle 130 may be greater than seven to one. The heater 134 may be square, with each side having a length 147. The length may be 47 microns, 51 microns, or 71 microns. This would have an area of 2209, 2601, or 5041 microns square, respectively. If the nozzle diameter is 20 microns, an area at the second end would be 314 microns square, giving an approximate ratio of 7 to 1, 8 to 1, or 16 to 1, respectively.

Figure 15:
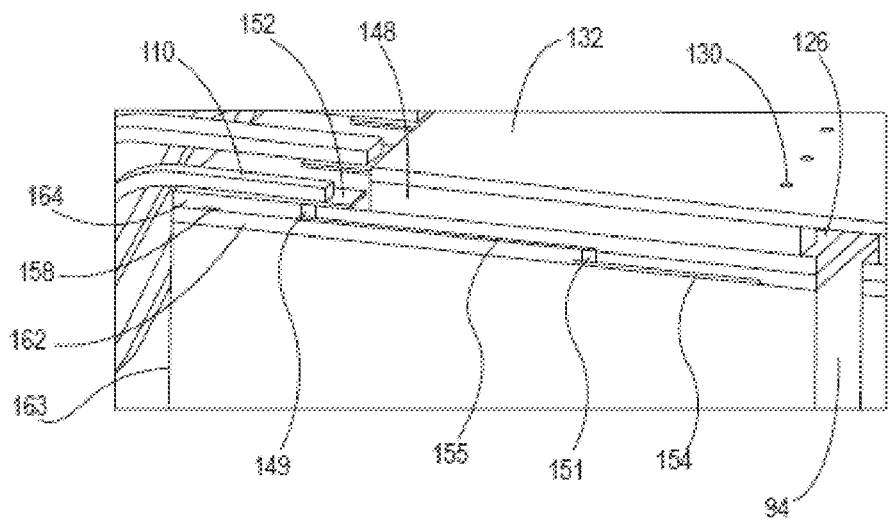
FIG. 15 is a sectional view of FIG. 9 taken along line 15-15.

With reference to FIG. 15, a length of the first contact 154 can be seen adjacent to the inlet 94. A via 151 couples the first contact 154 to trace 155 that is formed on the first dielectric layer 162. The second dielectric layer 164 is on the trace 155. A via 149 is formed through the second dielectric layer 164 and couples the trace 155 to the contact pad 152. A portion of the ground line 158 is visible toward an edge 163 of the die, between the via 149 and the edge 163.

As can be seen in this cross-section, the die 92 may be relatively simple and free of complex integrated circuitry. This die 92 will be controlled and driven by an external microcontroller or microprocessor. The external microcontroller or microprocessor may be provided in the housing. This allows the PCB 106 and the die 92 to be simplified and cost effective. There may be two metal or conductive levels formed on the substrate. These conductive levels include the contact 154 and the trace 155. All of these features can be formed on a single metal level. This allows the die to be simple to manufacture and minimizes the number of layers of dielectric between the heater and the chamber.

In use, when the fluid composition in each of the chambers is heated by the heating element, the fluid composition vaporizes to create a bubble. The expansion that creates the bubble causes fluid composition to eject from the nozzle 130 and to form a plume of one or more droplets.

Sensors

The delivery system may include commercially available sensors that respond to environmental stimuli such as light, noise, motion, and/or odor levels in the air. For example, the delivery system can be programmed to turn on when it senses light, and/or to turn off when it senses no light. In another example, the delivery system can turn on when the sensor senses a person moving into the vicinity of the sensor. Sensors may also be used to monitor the odor levels in the air. The odor sensor can be used to turn-on the delivery system, increase the heat or fan speed, and/or step-up the delivery of the fluid composition from the delivery system when it is needed.

VOC sensors can be used to measure intensity of perfume from adjacent or remote devices and alter the operational conditions to work synergistically with other perfume devices. For example a remote sensor could detect distance from the emitting device as well as fragrance intensity and then provide feedback to device on where to locate device to maximize room fill and/or provide the "desired" intensity in the room for the user.

The devices may communicate with each other and coordinate operations in order to work synergistically with other perfume devices.

The sensor may also be used to measure fluid composition levels in the reservoir or count firing of the heating elements to indicate the cartridge's end-of-life in advance of depletion. In such case, an LED light may turn on to indicate the reservoir needs to be filled or replaced with a new reservoir.

The sensors may be integral with the delivery system housing or in a remote location (i.e. physically separated from the delivery system housing) such as remote computer or mobile smart device/phone. The sensors may communicate with the delivery system remotely via low energy blue tooth, 6 low pan radios or any other means of wirelessly communicating with a device and/or a controller (e.g. smart phone or computer).

The user may be able to change the operational condition of the device remotely via low energy blue tooth, or other means.

Smart Chip

The cartridge 26 may include a memory in order to transmit optimal operational condition to the device.

Microfluidic Die Operating Conditions

The drive circuitry is powered by about 4 to about 24 Volts, or about 4 to about 16 Volts from an external power source. The heating element 134 is electrically connected to a microprocessor, which may be part of the device or cartridge and comprises software programmed to control operation of the heating element 134 such as firing time, firing sequence, and frequency of the heating element. When the heating element 134 is activated under the direction of the software, the fluid composition emits from the nozzles 130.

Figure 19:
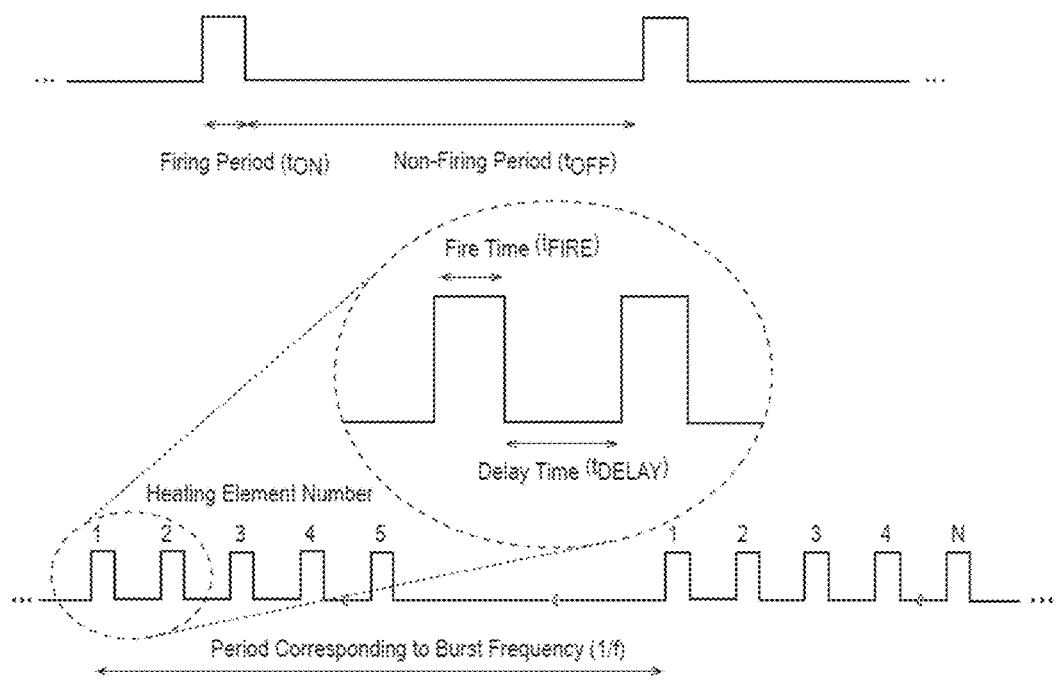
FIG. 19 is a diagram of wave forms and pulse timings of electrical signals of a microfluidic die.

Referring to FIG. 19, the microprocessor supplies firing pulses having a fire time (denoted $t_{FIRE}$) to a heating element 134. In some embodiments as shown in FIG. 19, a plurality of individual heating elements are fired sequentially (1, 2, 3, 4, etc), with an interposed delay time (denoted $t_{DELAY}$), in a sequence referred to as a burst. Bursts occur at a burst frequency (denoted $f_{BURST}$) of about 100 to about 8000 Hertz, or about 100 to about 6000 Hertz, or about 1000 to about 6000 Hertz, or about 1000 to about 5000 Hertz, or about 2000 to 5000 Hertz or about 1000 to about 2500 Hertz, during a firing period (denoted $t_{ON}$). In an embodiment where heating elements 134 are configured to be fired sequentially, the burst frequency ($f_{BURST}$) is equivalent to the firing frequency of an individual nozzle.

It has been found that the firing frequency will impact droplet size as well as how far upward the droplet is ejected which is important for avoiding deposition. With higher rates (e.g. 5000 Hertz), the droplets are fired at 5000 times/second which provides more momentum for the following droplets and hence causes the droplets to be ejected further which may help reduce deposition on surrounding surfaces. In addition, at 5000 Hertz the droplets are smaller for a given chamber size due to insufficient time to completely fill the chamber which has been defined above as refill limited mode.

The firing period ($t_{ON}$) may have a duration of about 0.25 seconds to about 10 seconds, or about 0.5 seconds to about 2 seconds, or about 0.25 seconds to about 1 second. A non-firing period (denoted $t_{OFF}$)—where no firing pulses are supplied to the heating element 134, may have a duration of about 9 seconds to about 200 seconds. When in a continuous repeat mode the $t_{ON}$ and $t_{OFF}$ are repeated continuously over an extended period of time to deliver a desired mg/hr rate of fluid. For example, with a burst frequency of 5000 Hertz and a firing period ($t_{ON}$) of 0.5 seconds, each nozzle is firing 2500 times during that sequence. If the $t_{OFF}$ is 10 seconds, then the sequence will be repeated every 10.5 seconds or about 6 times/minute and the total firings of each nozzle would be 2500 multiplied by about 6 times/min or about 15,000 firings/min. This delivery rate, per table 1, with 20 nozzles firing will deliver about 90 mg/hour of fluid composition into the air.

In another example of continuous repeat mode at 5000 Hz, to deliver 5 mg/hr of fluid composition, the heating element 134 may have firing periods ($t_{ON}$) and non-firing periods ($t_{OFF}$) comprising a 0.3% duty cycle (e.g. 0.5 second firing and 160 seconds non-firing). To deliver 57 mg/hr, the heating element may have firing and non-firing periods comprising a 2.4% duty cycle (e.g. 0.5 second firing and 20 seconds non-firing). In the case of an electromechanical actuator as the activation element, the stated heating element could be a piezo element. FIG. 19 show a firing pattern for the heating element 134 of the 1 to 2 microsecond pulse is repeated at the rates below to achieve intensity levels from level 1 to level 10 (or 5 to 90 mg/hr).

Housing

With reference to FIGS. 1-3, the microfluidic delivery system 10 may include a housing 12. The housing 12 may be constructed from a single component or have multiple components that are combined to form the housing 12. The housing 12 may be defined by an interior 21 and an exterior 23. The housing 12 may be comprised of an upper portion 14, a lower portion 16, and a body portion 18 that extends between and connects the upper portion 14 and the lower portion 16.

The housing 12 may include an opening 20 in the upper portion 14 of the housing 12 and a holder 24 for receiving and holding the cartridge 26 in the housing 12. The cartridge 26 may be received into the upper portion 14 of the housing 12.

The microfluidic delivery system 10 may comprise a fan to assist in driving room-fill and/or to help avoid deposition of larger droplets from landing on surrounding surfaces of the device that could damage the surface.

The microfluidic delivery system 10 may be in electrical communication with a power source. The power source may be located in the interior 21 of the housing 12, such as a disposable battery or a rechargeable battery. Or, the power source may be an external power source such as an electrical outlet that connects with a power cord 39 connected with the housing 12. The housing 12 may include an electrical plug that is connectable with an electrical outlet. The microfluidic delivery system may be configured to be compact and easily portable. As such, the power source may include rechargeable or disposable batteries. The microfluidic delivery system may be capable for use with electrical sources as 9-volt batteries, conventional dry cells such as "A", "AA", "AAA", "C", and "D" cells, button cells, watch batteries, solar cells, as well as rechargeable batteries with recharging base.

Figure 16:
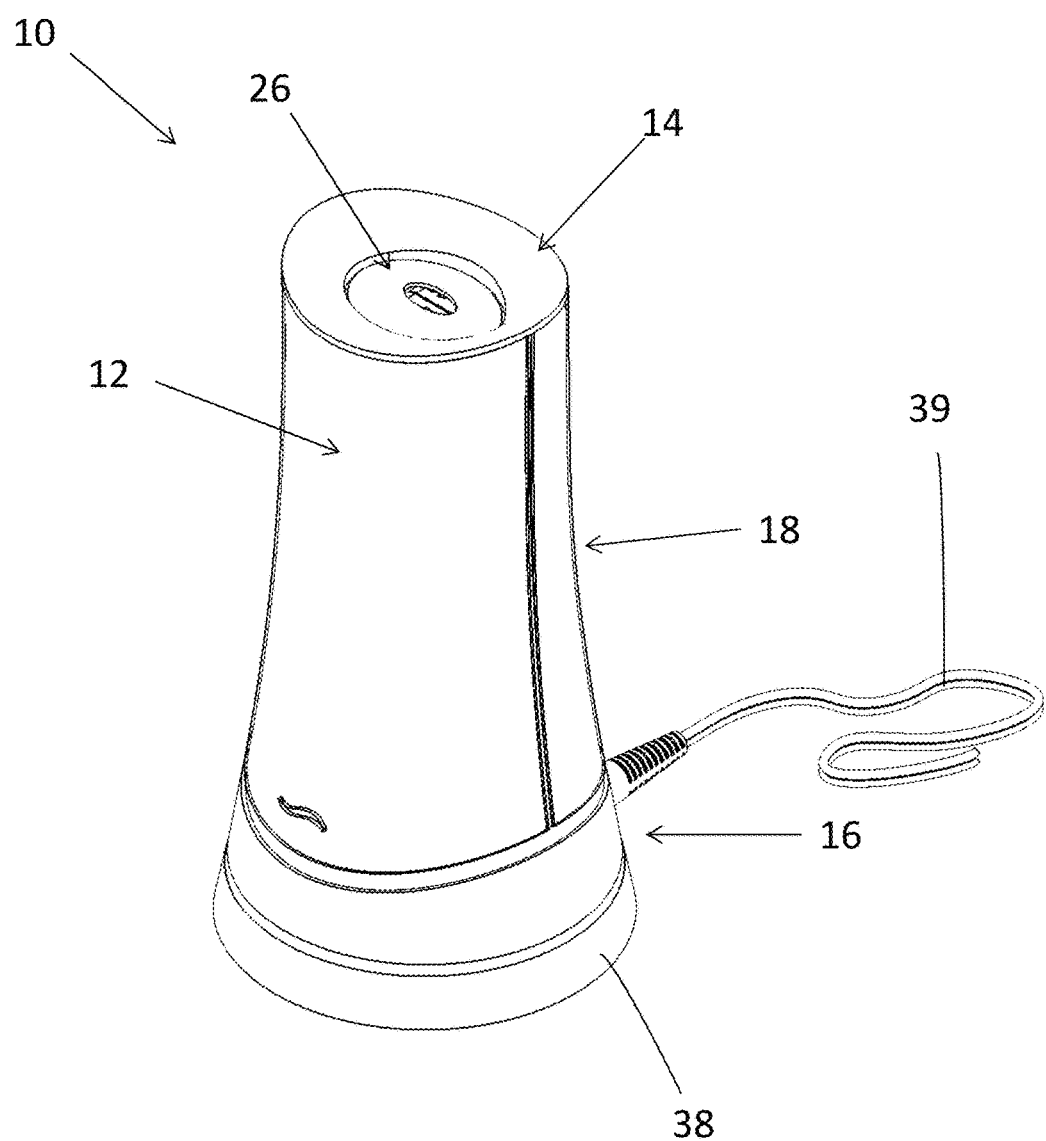
FIG. 16 is a perspective view of a microfluidic delivery system including a housing having a cartridge disposed therein and a charger for recharging rechargeable batteries used to power the microfluidic delivery system.

With reference to FIG. 16, the microfluidic delivery system 10 may be powered by rechargeable batteries connected with the housing. The rechargeable batteries may be charged using a charger 38. The charger 38 may include an electrical power connection 39 that connects with an external power source, such as an electrical outlet or battery terminals. The charger 38 may receive the housing 12 to charge the batteries. The electrical contacts 48 disposed on the interior 21 of the housing couple with the internal or external power source and couple with electrical contacts on the microfluidic delivery member of the cartridge to power the die. The housing 12 may include a power switch on exterior 23 of the housing 12.

Figure 17:
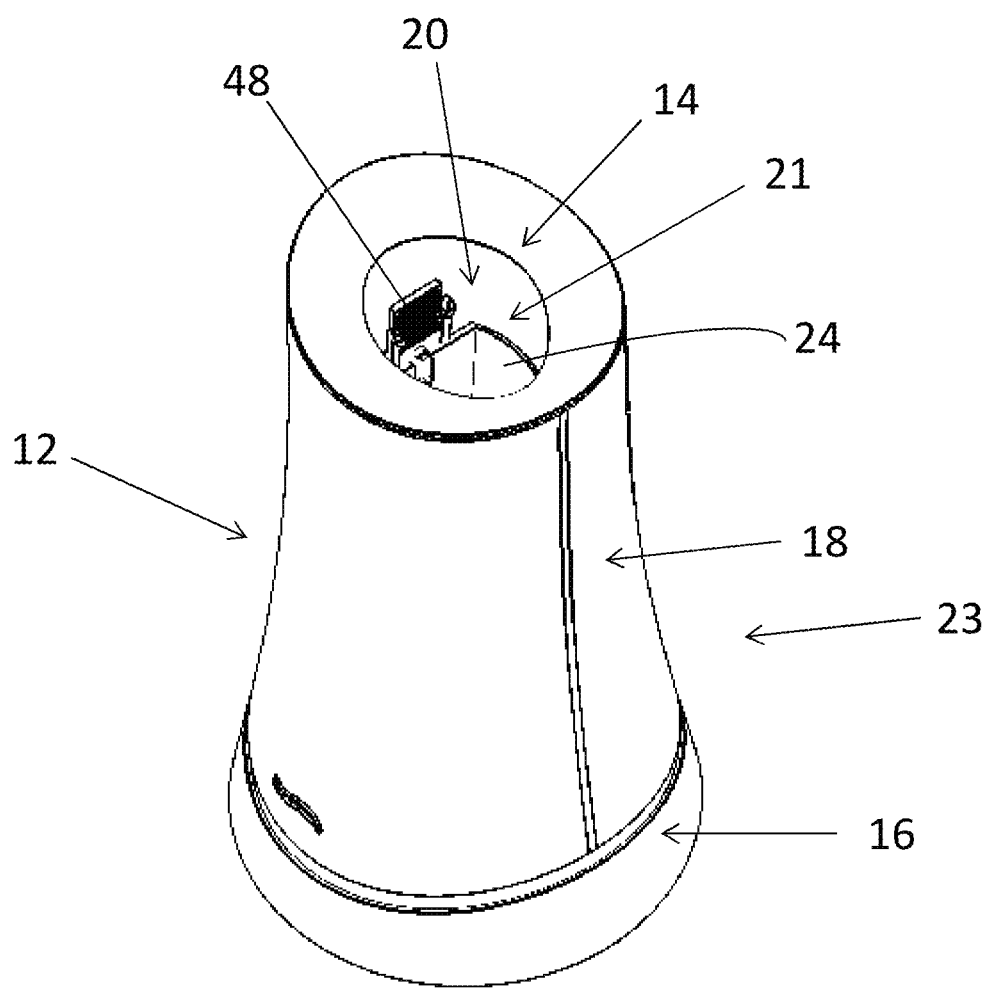
FIG. 17 is a perspective view of the housing of the microfluidic delivery system of FIG. 16 without a charger or cartridge connected therewith.
Figure 18:
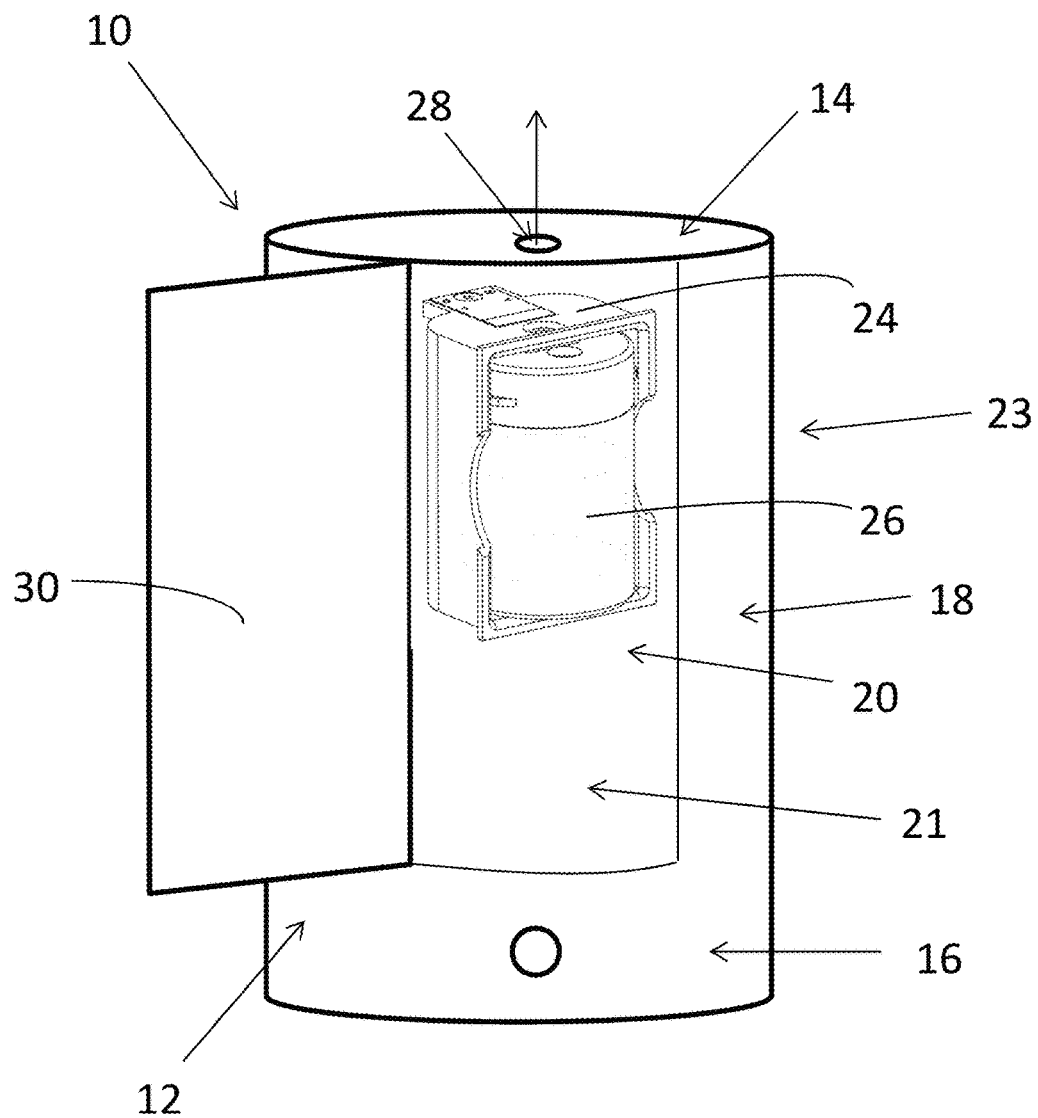
FIG. 18 is a schematic, perspective view of a housing having a cartridge disposed therein, and comprising a door for accessing the interior of the housing.

The opening 20 may be disposed in various locations of the housing 12. With reference to FIG. 17, the opening 20 may be disposed in the upper portion 14 of the housing 12. With reference to FIG. 18, the opening 20 may be disposed in the body portion 18 of the housing 12. The housing 12 may include a door 30 or structure to cover the opening 20. The cartridge 26 may slide in through the opening in the body portion 18 of the housing 12. The housing 12 may include air outlet 28 that places an environment on the exterior 23 of the housing 12 in fluid communication with the interior 21 of the housing 12. The door 30 may rotate to provide access to the air outlet 28. However, it is to be appreciated that the door or covering may be configured in various different ways. The door 30 may form a substantially air tight connection with the remainder of the housing 12 such that pressurized air in the interior 21 of the housing 12 does not escape through any gaps between the door 30 and the housing.

A fan 32 may direct air through the air flow path 46 as the die 92 dispenses a portion of fluid composition into the air, causing the fluid composition 52 to exit through the orifice 42 of the outer cover 40. The air flow from the fan 32 may additional force to carry the dispensed fluid composition 52 into the air, which, in turn, can increase room fill, and/or decrease deposition, and/or direct the fluid composition to the desired target.

Methodologies

Composition Preparation: Compositions Containing Perfume and Propylene Glycol

Acquire 250 ml glass beaker and add perfume, at the weight specified in the example. Insert a magnetic stir bar into the beaker, and place the beaker onto a magnetic stir plate. Turn on the magnetic stir plate to a sufficient speed (for example, 500 rpm) to ensure vortex mixing without excessive foam. Add propylene glycol, at the weight specified in the example, to the vortex slowly until clear. Allow to mix for 10-30 minutes.

Composition Preparation: Compositions Containing Perfume, Propylene Glycol, and Distilled Water Acquire 250 ml glass beaker and add the propylene glycol, at the weight specified in the example, and add distilled water, at the weight specific in the example. Add perfume, at the weight specified in the example, into a separate 250 ml glass beaker glass. Insert a magnetic stir bar into the beaker containing the perfume and place the beaker onto a magnetic stir plate. Turn on the magnetic stir plate to a sufficient speed (for example, 500 rpm) to ensure vortex mixing without excessive foam. Add the propylene glycol and water mixture to the vortex slowly until clear. Allow to mix for 10-30 minutes.

Spray Rate Method

Acquire a die having the following dimensions:

Number of nozzles: 20, with each nozzle associated with an individual chamber

Chamber area=40 micron×40 microns

Height of each chamber=10 microns

Orifice diameter of each nozzle=25 microns

When the device is turned on, the operating conditions are as follows:

Power=14 volts

Burst Frequency=3000 Hz

Fire time=2.1 microseconds

On time=0.5 seconds ("firing period") (total of 3000*0.5*20=# of drops fired per burst)

Off time between firing periods=10 seconds

Place the weighed refill into the device. Record the starting time the device is turned on. After a period of time (minimum 2 hours) remove the refill then weigh again and record the stop time. Subtract the initial weight from the final weight to determine the amount dispensed. Divide the amount dispensed by the amount of time between measurements to calculate the average mg/hour over that time period.

EXAMPLES

Properties of Fragrance Compositions Used in the Examples.

Fragrance Composition 1:

| | |
|---|---|
| Mole Weighted Average cLogP (ACD Model) | 2.7 |
| Mole Weighted Average Boiling Point (ACD Model) | 219° C. |
| Measured Boiling Point | 209° C. |

Fragrance Composition 2:

| | |
|---|---|
| Mole Weighted Average cLogP (ACD Model) | 2.9 |
| Mole Weighted Average Boiling Point (ACD Model) | 229° C. |
| Measured Boiling Point | 202° C. |

Fragrance Composition 3:

| | |
|---|---|
| Mole Weighted Average cLogP (ACD Model) | 2.1 |
| Mole Weighted Average Boiling Point (ACD Model) | 273° C. |
| Measured Boiling Point | TBD |

Fragrance Composition 4:

| | |
|---|---|
| Mole Weighted Average cLogP (ACD Model) | 3.0 |
| Mole Weighted Average Boiling Point (ACD Model) | 207° C. |
| Measured Boiling Point | TBD |

Fragrance Composition 5:

| | |
|---|---|
| Mole Weighted Average cLogP (ACD Model) | 3.8 |
| Mole Weighted Average Boiling Point (ACD Model) | 259° C. |
| Measured Boiling Point | TBD |

Examples A-E: C Log P and Water Stability The following examples in Table 4 demonstrate the effect of C log P of the fragrance composition on the ability of the composition to form clear, stable mixtures with water.

TABLE 4 cLogP and Water Stability of Examples A-E

| Example | Fragrance Composition | Fragrance CLogP | Propylene Glycol wt % | Water wt % | Mixture clarity/ homogeneity |
|---|---|---|---|---|---|
| A1 | Composition 1 | 2.74 | 5 | 2 | Clear |
| A2 | Composition 1 | 2.74 | 4 | 1 | Clear |
| B1 | Composition 2 | 2.9 | 8 | 2 | Hazy, turning clear |
| B2 | Composition 2 | 2.9 | 4 | 1 | Clear |
| C1 | Composition 3 | 2.1 | 8 | 2 | Clear |
| D1 | Composition 4 | 3.0 | 8 | 2 | Hazy |
| D2 | Composition 4 | | 5 | 2 | Hazy |
| E1 | Composition 5 | 3.8 | 8 | 2 | Phase separation |
| E2 | Composition 5 | 3.8 | 5 | 2 | Hazy |
| E3 | Composition 5 | | 4 | 1 | Clear |

Note from Examples A-E that fragrance compositions with c Log P <2.5 show clear solutions when mixed with 2.0 wt % water while fragrance compositions with c log P>3.0 show hazy or phase-separated mixtures when combined with 2.0 wt % water. Fragrance composition with c Log P between about 2.5 and 3.0 form either hazy and clear compositions when combined with 2.0 wt % water.

Figure 20:
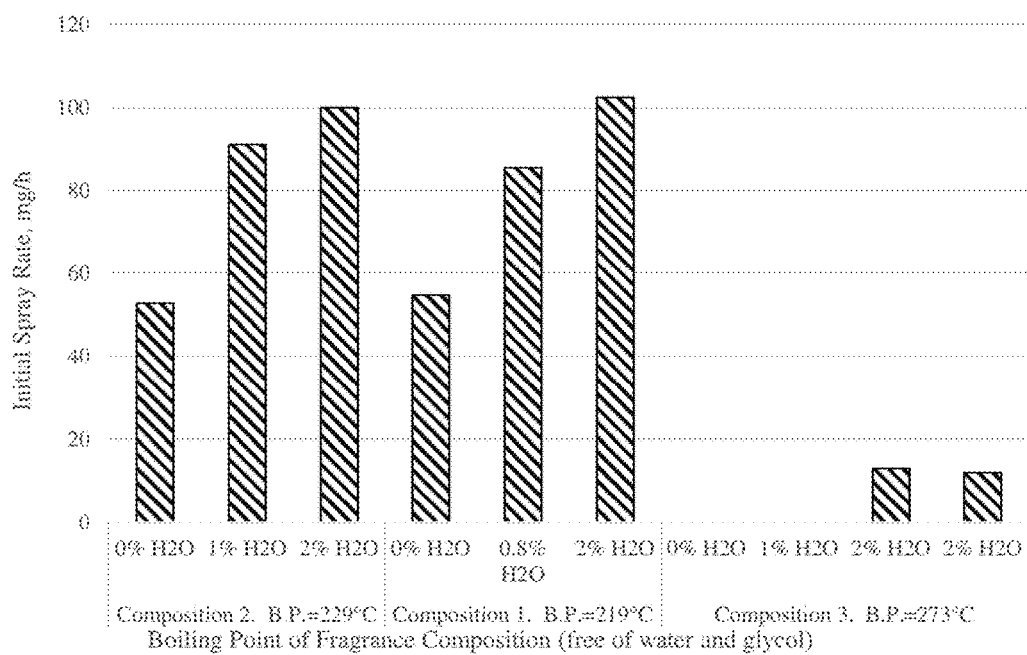
FIG. 20 is a plot that illustrates the effect of the perfume mixture boiling point and water level on the initial spray rate.

As shown in Table 5 and FIG. 20, Examples 1-9, taken together, indicated that adding water and having a B.P. less than about 250 C increase spray rate from the microfluidic die-based delivery system.

TABLE 5

Examples 1-9: Water and Glycol Compositions and Performance

| | Ex. 1 | Ex. 2 | Ex. 3 | Ex. 4 | Ex. 5 | Ex. 6 | Ex. 7 | Ex. 8 | Ex. 9 |
|---|---|---|---|---|---|---|---|---|---|
| Composition 1 | 100 | 95 | 95 | 93 | | | | | |
| Composition 2 | | | | | 95 | 95 | 90 | | |
| Composition 3 | | | | | | | | 95 | 90 |
| Propylene Glycol | 0 | 5 | 4.2 | 5.0 | 5 | 4 | 8 | 4 | 8 |
| Water wt % | 0 | 0 | 0.8 | 2.0 | 0 | 1 | 2 | 1 | 2 |
| Spray Rate (mg/h) | 51.4 | 54.8 | 85.6 | 102.5 | 52.8 | 91.3 | 100 | 0 | 13 |

Figure 21:
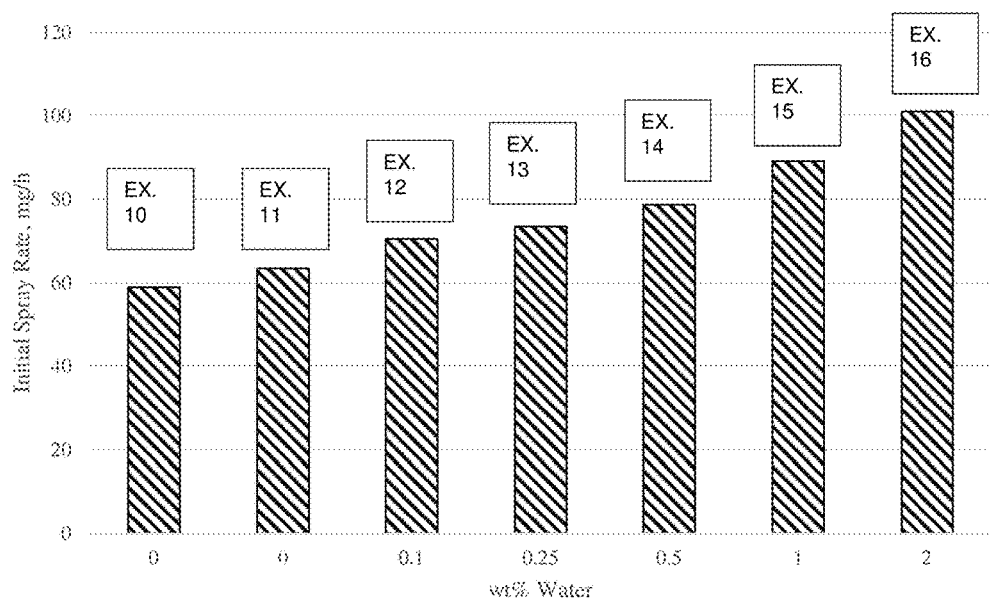
FIG. 21 is a plot showing the effect of water on the spray rate of a composition comprising a perfume mixture.

As shown in Table 6 and FIG. 21, Examples 10-16 show that adding water to a fragrance composition at levels from 0.1% to 2.0% by weight beneficially increases spray performance from a microfluidic dye.

TABLE 6

Examples 10-16

| | Ex. 10 | Ex. 11 | Ex. 12 | Ex. 13 | Ex. 14 | Ex. 15 | Ex. 16 |
|---|---|---|---|---|---|---|---|
| Composition 2 | 90 | 95 | 95.9 | 95.75 | 95.5 | 95 | 90 |
| Propylene Glycol | 10 | 5 | 4 | 4 | 4 | 4 | 8 |
| Water wt % | 0 | 0 | 0.1 | 0.25 | 0.5 | 1 | 2 |
| Spray Rate (mg/h) | 59 | 63.5 | 70.5 | 73.5 | 78.7 | 89.1 | 101 |

As shown in Table 7, Examples 17-21 demonstrate that adding water to a fragrance composition at levels up to 7% by weight beneficially increases spray performance from a microfluidic dye.

TABLE 7

Examples 17-21

| | Ex. 17 | Ex. 18 | Ex. 19 | Ex. 20 | Ex. 21 |
|---|---|---|---|---|---|
| Composition 3 | 95 | 95 | 90 | 92 | 83 |
| Propylene Glycol | 5 | 4 | 8 | 4 | 10 |
| Water wt % | 0 | 1 | 2 | 4 | 7 |
| Stability | clear | clear | clear | clear | ? |
| Spray Rate (mg/h) | 0 | 0 | 13 | 23 | 12 |

Throughout this specification, components referred to in the singular are to be understood as referring to both a single or a plurality of such component.

All percentages stated herein are by weight unless otherwise specified.

Every numerical range given throughout this specification will include every narrower numerical range that falls within such broader numerical range, as if such narrower numerical range were all expressly written herein. For example, a stated range of "1 to 10" should be considered to include any and all subranges between (and inclusive of) the minimum value of 1 and the maximum value of 10; that is, all subranges beginning with a minimum value of 1 or more and ending with a maximum value of 10 or less, e.g., 1 to 6.1, 3.5 to 7.8, 5.5 to 10, etc.

Further, the dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A cartridge comprising a microfluidic die and a fluid composition in fluid communication with the microfluidic die, the fluid composition comprising:
    about 50 wt. % to about 100 wt. % of a perfume mixture, by weight of the overall composition, wherein the perfume mixture has a mol-weighted average C log P of less than or equal to about 2.9;
    an oxygenated solvent selected from the group consisting of: a polyol, glycol ether, polyether, or combination thereof; and
    about 0.25 wt. % to about 9.5 wt. % water, by weight of overall composition.

2. The cartridge of claim 1, wherein the mol-weighted average boiling point of the perfume mixture is less than 250° C.

3. The cartridge of claim 1, wherein the perfume mixture has a mol-weighted average C log P of less than or equal to about 2.5.

4. The cartridge of claim 1 comprising about 0.25 wt. % to about 7.0 wt. % water, by weight of the overall composition.

5. The cartridge of claim 1, wherein the fluid composition is substantially free of suspended solids.

6. The cartridge of claim 1, wherein the oxygenated solvent is a polyol.

7. The cartridge of claim 6, wherein the oxygenated solvent is a glycol ether.

8. The cartridge of claim 1, wherein the oxygenated solvent is present at a level of about 0.01 wt. % to about 20 wt. %, by weight of the overall composition.

9. The cartridge of claim 1, wherein the microfluidic die comprises a heater.

10. A microfluidic delivery system comprising a housing and a cartridge that is connectable with the housing, wherein the cartridge comprises a reservoir for containing a fluid composition, a microfluidic die, and a fluid transport member configured to deliver the fluid composition from the reservoir to the microfluidic die, wherein the fluid composition comprises:
    about 50 wt. % to about 100 wt. % of a perfume mixture, by weight of the overall composition, wherein the perfume mixture has a mol-weighted average C log P of less than or equal to about 2.9;
    an oxygenated solvent selected from the group consisting of: a polyol, glycol ether, polyether, or combination thereof; and
    about 0.25 wt. % to about 9.5 wt. % water, by weight of overall composition.

11. The microfluidic delivery system of claim 10, wherein the mol-weighted average boiling point of the perfume mixture is less than 250° C.

12. The microfluidic delivery system of claim 10, wherein the perfume mixture has a mol-weighted average C log P of less than or equal to about 2.5.

13. The microfluidic delivery system of claim 10 comprising about 0.25 wt. % to about 7.0 wt. % water, by weight of the overall composition.

14. The microfluidic delivery system of claim 10, wherein the oxygenated solvent is a polyol.

15. The microfluidic delivery system of claim 10, wherein the oxygenated solvent is present at a level of about 0.01 wt. % to about 20 wt. %, by weight of the overall composition.

16. A method of dispensing a fluid composition from a microfluidic die, the method comprising the steps of:
    comprising a housing and a cartridge that is connectable with the housing, wherein the cartridge comprises a reservoir, a fluid transport member, a fluid composition, and a microfluidic die, the fluid composition comprising:
        about 50% to about 100%, by weight of the fluid composition, of a perfume mixture, wherein the perfume mixture has an average C log P of less than about 2.9;
        an oxygenated solvent selected from the group consisting of: a polyol, glycol ether, polyether, or combination thereof; and
        about 0.25 wt. % to about 7 wt. %, by weight of the fluid composition, of water.

17. The method of claim 16, wherein the mol-weighted average boiling point of the perfume mixture is less than 250° C.

18. The method of claim 16, wherein the perfume mixture has a mol-weighted average C log P of less than or equal to about 2.5.

19. The method of claim 16 comprising about 0.25 wt. % to about 7.0 wt. % water, by weight of the overall composition.

20. The method of claim 16, wherein the oxygenated solvent is present at a level of about 0.01 wt. % to about 20 wt. %, by weight of the overall composition.

* * * * *